(12) United States Patent
Ostroff et al.

(10) Patent No.: US 9,242,857 B2
(45) Date of Patent: Jan. 26, 2016

(54) YEAST CELL WALL PARTICLES FOR RECEPTOR-TARGETED NANOPARTICLE DELIVERY

(75) Inventors: Gary R. Ostroff, Worcester, MA (US); Ernesto Soto, Worcester, MA (US)

(73) Assignee: University of Massachusetts, Boston, MA (US)

( * ) Notice: Subject to any disclaimer, the term of this patent is extended or adjusted under 35 U.S.C. 154(b) by 1005 days.

(21) Appl. No.: 13/210,047

(22) Filed: Aug. 15, 2011

(65) Prior Publication Data
US 2012/0070376 A1 Mar. 22, 2012

Related U.S. Application Data

(60) Provisional application No. 61/373,828, filed on Aug. 14, 2010.

(51) Int. Cl.
| | | |
|---|---|---|
| *A61K 9/14* | (2006.01) | |
| *B82Y 5/00* | (2011.01) | |
| *A61K 9/50* | (2006.01) | |
| *A61K 9/51* | (2006.01) | |
| *A61K 47/48* | (2006.01) | |
| *A61K 35/66* | (2015.01) | |

(52) U.S. Cl.
CPC ............... *B82Y 5/00* (2013.01); *A61K 9/5068* (2013.01); *A61K 9/5115* (2013.01); *A61K 47/489* (2013.01); *A61K 47/4893* (2013.01); *A61K 47/48853* (2013.01); *A61K 35/66* (2013.01)

(58) Field of Classification Search
CPC ...................................................... A61K 35/66
See application file for complete search history.

(56) References Cited

U.S. PATENT DOCUMENTS

2005/0281781 A1    12/2005    Ostroff

OTHER PUBLICATIONS

International Search Report for International Application No. PCT/US2011/0147776, mailed Dec. 1, 2011 (4 pages).
Written Opinion of the International Searching Authority for International Application No. PCT/US2011/0147776, Feb. 2013 (4 pages).
Soto et al. 'Characterization of multilayered nanoparticles encapsulated in yeast cell wall particles for DNA delivery.' Bioconjugate Chemistry. 2008, vol. 19, No. 4, pp. 840-848.
Soto et al. 'Glucan particles for macrophage targeted delivery of nanoparticles.' Journal of Drug Delivery. 2011, vol. 2012.

*Primary Examiner* — Paul Dickinson
(74) *Attorney, Agent, or Firm* — Lathrop & Gage LLP; James H. Velema, Esq.

(57) ABSTRACT

The present invention generally relates to yeast cell wall microparticles loaded with nanoparticles for receptor-targeted nanoparticle delivery. In particular, the present invention relates to trapping nanoparticles either on the surface or inside a yeast glucan particles, for example, yeast glucal particles. The present invention further relates to methods of making the yeast cell wall particles loaded with nanoparticles. The present invention also relates to methods of using the yeast cell wall particles loaded with nanoparticles for receptor-targeted delivery of the nanoparticles, e.g., drug containing nanoparticles.

15 Claims, 15 Drawing Sheets

FIG. 1

GP encapsulation of small NPs (<30 nm)

1.
2. Crosslinking polymer

GP → GP-NP

Binding of large NPs to surface derivatized GPs

GP → Cationic or anionic polymer → Surface derivatized GP → NP-GP

Covalent coupling of cationic polymers to GP via reductive amination

1. KIO$_4$
2. Cationic polymer
3. NaBH

GP surface with cationic polymers
TP-GPs (i.e PEI, poly-L-lysine, chitosan)

Non-covalent binding of 200 nm rhodamine carboxylated Polystyrene nanoparticles (Invitrogen) to TP-GPs 200 nm rhodamine carboxylated polystyrene particles

YEAST CELL WALL PARTICLES FOR RECEPTOR-TARGETED NANOPARTICLE DELIVERY

RELATED APPLICATIONS

This application claims priority to U.S. Provisional Patent Application No. 61/373,828, filed Aug. 14, 2010. The entire content of the foregoing application is incorporated herein by reference.

STATEMENT AS TO FEDERALLY SPONSORED RESEARCH

This invention was made with government support under Grant No. DK085753 awarded by the National Institute of Diabetes and Digestive and Kidney Diseases, National Institutes of Health. The government has certain rights in the invention.

BACKGROUND OF THE INVENTION

Drug delivery systems are designed to provide a biocompatible reservoir of an active agent for the controlled release of the active agent dependent either on time, or on local conditions, such as pH. While macroscopic drug delivery systems such as transdermal patches, implantable osmotic pumps and implantable subcutaneous depots (e.g., NORPLANT™) have had some success, these technologies are often limited in, for example, achieving controlled dosing, compatibility with a variety of chemically distinct biomolecules, discomfort associated with administration and the like. Accordingly, there has been continuing interest in developing microscopic drug delivery systems aimed at overcoming some of the limitations inherent in the above described macroscopic systems.

In particular, there has been much recent research focused on developing novel microscopic drug delivery systems suitable for delivering therapeutic substances (e.g., drugs) in such a manner so as to get optimum benefits, including, for example, controlled release dosage forms, sustained release dosage forms, and the like. One such approach is using microencapsulation, e.g., microspheres or microcapsules, as carriers for drugs. Microencapsulation is a process whereby therapeutic substances, for example, small liquid droplets, are surrounded and enclosed by an intact shell. Microencapsulation is a particularly useful technology as it can be used to modify, delay and/or direct drug delivery and release following administration. A well-designed drug delivery system can overcome several of the problems of conventional therapy and enhance the therapeutic efficacy of a particular drug. It is the reliable means to deliver efficacious and effective dosages of drugs to appropriate target sites with specificity without untoward effects that has focused much attention to microencapsulation techniques as vital tools in drug delivery. These techniques obtain maximum therapeutic efficacy, as it becomes possible to deliver the agent to the target tissue in the optimal amount in the right period of time there by causing little toxicity and minimal side effects.

Microencapsulation provides a simple and cost-effective way to enclose bioactive materials, such as drugs, within a biocompatible coating or membrane for the purpose of protecting the bioactive materials and releasing the enclosed substances or their products in a controlled fashion. Microencapsulation techniques include, for example, natural and/or biodegradable polymers, polysaccharides, dendrimers, liposomes, micelles, optionally in functionalized forms, and other such biocompatible materials.

Microcapsules and microspheres are usually powders consisting of spherical particles 2 millimeters or less in diameter, usually 500 microns or less in diameter. If the particles are less than 1 micron, they are often referred to as nanocapsules or nanospheres. A description of methods of making and using microspheres and microcapsules can be found, for example in U.S. Pat. No. 5,407,609. Microcapsules and microspheres can be distinguished from each other by whether the active agent is formed into a central core surrounded by an encapsulating structure, such as a polymeric membrane, or whether the active agent is dispersed throughout the particle; that is, the internal structure is a matrix of the agent and excipient, usually a polymeric excipient. The release of the active agent from a microcapsule is often regulated by the biodegradation of the matrix material, usually a biodegradable polymeric material such as either poly(DL-lactide) (DL-PL) or poly(DL-lactide-co-glycolide) (DL-PLG) as the polymeric excipient.

Liposomes can be considered microcapsules in which the active agent core is encompassed by a lipid membrane instead of a polymeric membrane. Liposomes are artificial lipid vesicles consisting of lipid layers, where the active agent may be encapsulated inside the aqueous compartment of the liposome, or associated with the liposome on the surface via surface-coupling techniques. Liposomes can be prepared easily and inexpensively on a large scale and under conditions that are mild to entrapped active agents. They do not induce immune responses to themselves, and are used in humans for parenterally administered drugs.

While the high surface area/volume ratio of microcapsules, microspheres and liposomes favor the release of the active agent, their small size provides challenges in manufacturing. A wide variety of methods to prepare microcapsules and microspheres are described in the literature, e.g., U.S. Pat. No. 5,407,609. Several of these methods make use of emulsions to make microspheres, in particular to make microspheres less than 2 millimeters in diameter. To give a general example of such processes, one can dissolve a polymer in a suitable organic solvent (the polymer solvent), dissolve or disperse an agent in this polymer solution, disperse the resulting polymer/agent mixture into an aqueous phase (the processing medium) to obtain an oil-in-water emulsion with oil microdroplets dispersed in the processing medium, and remove the solvent from the microdroplets to form microspheres. These processes can also be performed with water-in-oil emulsions and with double emulsions. The use of emulsion-based processes that follow this basic approach is described in several U.S. patents, such as U.S. Pat. Nos. 3,737,337, 3,891,570, 4,384,975, 4,389,330, and 4,652,441.

As an alternative to traditional microencapsulation processes, yeast-based particles, or yeast microcapsules, can serve as readily available, biocompatible, biodegradable drug delivery particles. Yeast microcapsules are suitable for systemic drug delivery as well as oral, topical and inhalation mucosal drug delivery. Yeast microcapsules further have the ability to deliver therapeutic substances between cells to aid drug delivery.

The use of preformed natural microorganisms as microcapsules was first considered in the 1970s when it was observed that yeast cells (*Saccharomyces cerevisiae*), when treated with a plasmolyser, could be used to encapsulate water-soluble substances. When grown in fermenters, yeast microbial capsules reach a uniform size distribution and their physical makeup can be modified by simply altering the nutrient balance within the fermentation medium. In microencapsulation processes, the encapsulation can takes place in dead as well as live cells, indicating that encapsulation takes place by simple diffusion. Initial focus was on using yeast-based microencapsulation technology as a novel means of turning a volatile liquid into a powder for ease of handling. When it was observed that the yeast capsules released their payload on contact with the mucosal surfaces of the mouth more readily than in saliva alone, the possibility of targeted drug delivery using yeast cell capsules was first proposed.

Improved yeast microcapsule drug delivery systems are described for encapsulating and delivering a variety of soluble payload molecules including, but not limited to proteins, nucleic acids, antigens, small molecules, and the like. See, in particular U.S. Pat. No. 7,740,861, US 20050281781, US 20060083718, US 20080044438, US 20090209624, and US 20090226528. It is further desirable, however, to have the capability to encapsulate and deliver particulate payloads, such as, nanoparticles enabling a whole host of new functionalities in the field of drug delivery. In particular, nanoparticles have unusual properties that can be used to improve drug delivery, for example, facilitating cellular uptake, trafficking, regulating drug release, improving solubility, and the like.

The development of effective drug delivery systems presents multiple challenges, such as issues of drug solubility, targeting, in vivo stability and clearance, and toxicity. Nanotechnology-based drug delivery systems are a promising approach to fulfill the need for new delivery systems offering several advantages, such as high drug binding capacity due to their large surface area, improved solubility and bioavailability of hydrophobic drugs, extended drug half-life, improved therapeutic index, reduced immunogenicity, and the possibility for controlled release (S. S. Suri, et al., *J. Occupational Med. and Toxicol.*, vol. 2, pp. 1-6, 2007, R. A. Petros, et al., *Nature Reviews Drug Discovery*, vol. 9, pp. 615-627, 2010, E. Brewer, et al., *J. Nanomaterials*, vol. 2011, Article ID 408675, pp. 1-10, 2011). Nanoparticles can also be synthesized with control over average size, size distribution and particle shape, all key factors related to cellular uptake mechanisms and improved penetration across biological barriers. Additionally, some nanoparticles offer the possibility for combined use as therapeutic and diagnostic/imaging tools. A new term, theranostics, has been recently proposed to describe these types of nanoparticles (D. Sun, *Molecular Medicine*, vol. 7, no. 6, pp. 1879, 2010). The successful development of nanoparticle based delivery systems is exemplified by the use of nanomaterials for anticancer drug formulations (M. Ferrari, *Nature Reviews*, vol. 5, pp. 161-171, 2005, M. E. Davis, et al., *Nature Reviews Drug Discovery*, vol. 7, pp. 771-782, 2008).

A primary challenge to realizing the full promise of nanoparticle based drug delivery is the lack of optimal strategies to achieve selective and efficient cellular targeting. The mechanism of NP uptake is dependent on particle size and shape (D. E. Owens III, et al., *Int. J. Pharmacy*, vol. 307, pp. 93-102, 2006, J. A. Champion, et al., *J. Controlled Release*, vol. 121, pp. 3-9, 2007, F. Alexis, et al., *Molecular Pharmaceutics*, vol. 5, pp. 505-515, 2007), and several competing uptake mechanisms result in undesired processes including off-target accumulation in other organs tissues and cells, rapid clearance from in vivo circulation (especially nanoparticles less than 5 nm) (S. V. Vinogradov, et al., *Advanced Drug Delivery Reviews*, vol. 54, pp. 135-147, 2002, H. S. Choi, et al., *Nature Biotechnology*, vol. 25, pp. 1165-1170, 2007), opsonization and macrophage clearance (D. E. Owens III, et al., *Int. J. Pharmacy*, vol. 307, pp. 93-102, 2006, J. A. Champion, et al., *J. Controlled Release*, vol. 121, pp. 3-9, 2007, F. Alexis, et al., *Molecular Pharmaceutics*, vol. 5, pp. 505-515, 2007, S. V. Vinogradov, et al., *Advanced Drug Delivery Reviews*, vol. 54, pp. 135-147, 2002, H. S. Choi, et al., *Nature Biotechnology*, vol. 25, pp. 1165-1170, 2007, M. D. Howard, et al., *J. Biomedical Nanotechnology*, vol. 4, pp. 133-148, 2008), and complement activation by proteins that results in hypersensitivity reactions (I. Hamad, et al., *Molecular Immunology*, vol. 45, pp. 3797-3803, 2008). Nanoparticles can be somewhat targeted by attaching ligands with specificity to receptors that are overexpressed in certain cells (i.e., folate and transferrin receptors in cancer cells (Wang, et al., *ACSNano*, vol. 3, pp. 3165-3174, 2009, P. S. Low, et al., *Accounts of Chemical Research*, vol. 41, pp. 120-129, 2008, C. H. J. Choi, et al., *Proceedings of the National Academy of Sciences USA*, vol. 107, pp. 1235-1240, 2010, M. B. Dowling, et al., *Bioconjugate Chemistry*, vol. 21, pp. 1968-1977, 2010, L. Han, et al., *Molecular Pharmaceutics*, vol. 7, no. 6, pp. 2156-2165, 2010), or targeting cell populations with high selectivity by grafting specific targeting moieties to cell surface receptors known to be expressed only on target cells (i.e. antibodies to target prostate-specific membrane antigen (PSMA) (A. K. Patri, et al., *Bioconjugate Chemistry*, vol. 15, pp. 1174-1181, 2004) or galactose to target asialoglycoprotein receptors on hepatocyte cells (C. Plank, et al., *Bioconjugate Chemistry*, vol. 3, pp. 533-539, 1992). Some interfering processes can be reduced by coating the nanoparticles with a hydrophilic polymer (i.e. PEG polymer brush or Stealth nanoparticles). PEG is a non-immunogenic, non-toxic and protein-binding resistant polymer. PEG coating of nanoparticles prevents opsonization by shielding surface charges, reducing macrophage clearance, increasing steric repulsion of blood components, and increasing hydrophilicity and in vivo circulation of nanoparticles (M. D. Howard, et al., J. Biomedical Nanotechnology, vol. 4, pp. 133-148, 2008, K. G. Neoh, et al., *Polymer Chemistry*, vol. 2, pp. 747-759, 2011). Given the recent focus on nanoparticle-based delivery systems, for example, in drug delivery methodologies, there exists a need for improved systems capable of enhanced delivery, in particular, in therapeutic settings.

SUMMARY OF THE INVENTION

The present invention improves upon previously described yeast-based microencapsulation methodologies, in particular, by providing for the incorporation of nanoparticles into and/or onto yeast cell wall particles (YCWPs), for example, yeast glucan particles (microparticles) (YGPs). The improved technologies provide for delivery of nanoparticles, the nanoparticles themselves having utility in biomedical applications, or the nanoparticles imparting one or more functionalities of use in various biomedical, e.g., drug delivery applications.

In one aspect, the invention provides a yeast cell wall particle (YCWP), e.g., yeast glucan particle (YGP), delivery system, comprising yeast cell wall particles (YCWPs), e.g., YGPs, comprising nanoparticles having at least one dimension of about 1-40 nm (e.g., about 1-40, 2-40, 5-30, 10-30, 10-40 or 20-40 nm) within the interior of the YCWPs, wherein the YCWP delivery system is prepared by a process comprising the steps of:
  (a) loading the YCWPs, e.g., YGPs, with the nanoparticles by incubating together in suspension, e.g., for about 1-2 hours,
  (b) drying, e.g., lyophilizing, the material resulting from (a),
  (c) optionally repeating the loading and drying, e.g., lyophilizing, steps at least once, (d) resuspending the YCWPs, e.g., YGPs, and nanoparticles in solution, e.g., water, for a time sufficient to promote further entry of nanoparticles into the YCWPs, e.g., to "push" the nanoparticles into the YCWPs, (e) drying the material resulting from (d), and optionally (f) trapping the nanoparticles in the YCWPs, e.g., YGPs, using an appropriate trapping means, such that the YCWP delivery system is prepared.

Drying can be accomplished, for example, by evaporation, vacuum drying, lyophilization, mild heat, air drying, gas drying, freeze drying or any other means suitable for removing liquid reagents (e.g., buffer or solvent) from suspensions.

In another aspect, the invention provides, a yeast cell wall particle (YCWP), e.g., a yeast glucan particle (YGP) delivery system, comprising yeast cell wall particles (YCWPs), e.g., YGPs, comprising nanoparticles having at least one dimension of about 10-1000 (e.g., about 10-100, 100-500, 500-1000, preferably 30 nm or greater, e.g., 30-1000 nm), on the surface of the YCWPs, wherein the YCWP delivery system is prepared by a process comprising the steps of:

(a) obtaining YCWPs, wherein the surface of the YCWPs (e.g., YGPs) are derivitized and/or modified to facilitate nanoparticle (NP)-loading onto the surface, (b) incubating the YCWPs of step (a) with nanoparticles (NPs) together in suspension for a time sufficient to facilitate loading of the NPs onto the surface of the YCWPs, e.g., about 12-24 hours, and (b) washing and dispersing, e.g., sonicating, the material resulting from (b), such that the YCWP delivery system is prepared.

In exemplary embodiments, the YCWPs (e.g., YGPs), are surface-derivitized e.g., derivitized to have an electrostatic, e.g., cationic or anionic surface and the NPs are bound, e.g., electrostatically bound to the derivitized surface. In other exemplary embodiments, the YCWPs (e.g., YGPs) are surface modified, e.g., modified to facilitate covalent or affinity binding of the NPs to the surface. In one embodiment, the YCWPs (e.g., YGPs) are surface-modified to facilitate biotin-streptavidin binding of NPs to the surface. In another embodiment, the YCWPs (e.g., YGPs) are surface-modified to facilitate covalent binding of the NPs to the surface. In exemplary embodiments, YCWPs (e.g., YGPs) are surface-derivitized surface-modified to facilitate binding of the NPs to the surface. (e.g., electrostatically bound and/or affinity conjugated) to the surface.)

Each of the above exemplary methods can be used to load a variety of nanoparticles into or onto YCWPs (e.g., YGPs). In some embodiments, the nanoparticles can be quantum dots. In other embodiments, the nanoparticles can be magnetic particles. In other embodiments, the nanoparticles can be virus or virus-like particles, for example, for gene delivery applications. In some embodiments, the nanoparticles can be silica nanoparticles, e.g., mesoporous silica nanoparticles (MSNs). In some embodiments, nanoparticles include a payload. In some embodiments, YCWPs (e.g., YGPs) include nanoparticles and one or more payloads. In some embodiments, YCWPs (e.g., YGPs) include labeled nanoparticles and/or payloads In certain embodiments, the trapping means can be electrostatic trapping means. In various embodiments, the electrostatic trapping can result from interaction of the nanoparticle with a cationic polymeric trapping molecule, e.g., PEI.

In some embodiments, the trapping means can be through a physical trapping means. In certain embodiments, the physical trapping can result from interaction of the nanoparticle with a trapping molecule selected from the group consisting of tRNA, alginate, and chitosan. Other suitable trapping molecules are described in detail infra.

In some embodiments, the trapping means can be hydrophobic trapping means. In other embodiments, the trapping means can be affinity trapping means. Is still other embodiments, trapping means take advantage of more than one type of interaction property, for example, trapping means that have both an electrostatic and affinity property.

In some embodiments, more than one nanoparticle can be loaded into, onto, or into and onto a YCWP (e.g., YGP) of the invention. For example, magnetic nanoparticles can be loaded into a particle and on the surface of a particle, e.g., via a biotin:strepavidin means. In other embodiments, nanoparticles (one or more) can be loaded with soluble payloads (one or more, optionally polyplexed). Multilayered formats are readily within the scope of the invention. Soluble payload molecules can also be bound to, or embedded in nanoparticles of the invention. Without being bound in theory, it is believed that the self aggregation properties of nanoparticles can, in some instances, be beneficial in trapping nanoparticles within YCWPs (e.g., YGPs).

The foregoing description broadly describes the features and technical advantages of certain embodiments of the present invention. Further technical advantages will be described in the detailed description of the invention that follows. Novel features that are believed to be characteristic of the invention will be better understood from the detailed description of the invention when considered in connection with any accompanying figures and examples. However, the figures and examples provided herein are intended to help illustrate the invention or assist with developing an understanding of the invention, and are not intended to be definitions of the invention's scope.

BRIEF DESCRIPTION OF DRAWINGS

FIG. 1 schematically depicts exemplary nanoparticle (NPs) loading strategies inside or on the surface of glucan particles (GPs).

FIG. 6 graphically depicts nanoparticle binding to GP surface.

FIG. 9 depicts the characterization of GP formulations by Zeta Potential

DETAILED DESCRIPTION OF THE INVENTION

Figure 2A:
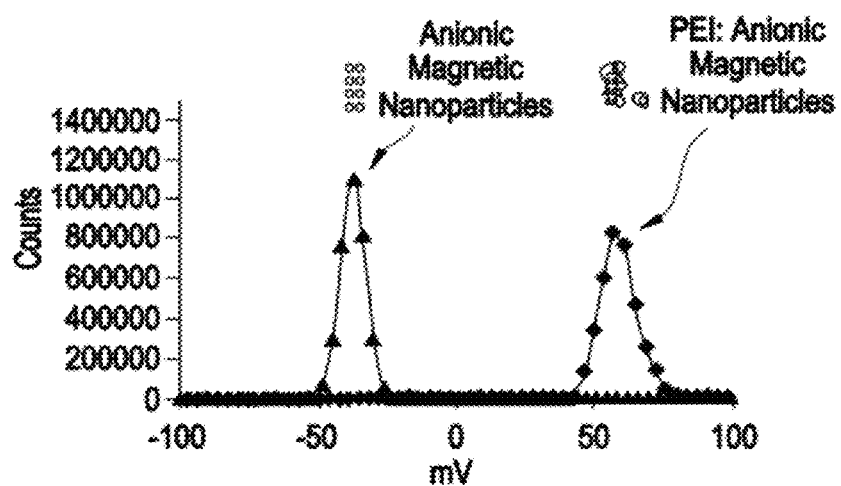
FIG. 2A graphically depicts characterization by Zeta potential of anionic magnetic nanoparticles with or without PEI.

The present inventors have developed a nanoparticle delivery system featuring yeast cell wall particles (YCWPs), e.g., yeast glucan particles (YGPs) (also referred to herein as glucal particles (GPs)), incorporating insoluble pre-formed nanoparticles (NPs) of, e.g., less than about 30 nm in diameter as cores inside the YCWPs, e.g., glucan particles (GP-NP), or nanoparticles electrostatically bound to the surface of derivatized YCWPs, e.g., glucan particles (NP-GP) (FIG. 1). The advantages of YCWP nanoparticle, e.g., YGP, nanoparticle, encapsulation include: (1) the encapsulation of payload complexes that cannot be prepared in situ as the synthetic conditions are not compatible with YCWPs, e.g., yeast glucan particles, (2) the loading of nanoparticles that can enhance the ability to load small drug molecules (neutral, hydrophobic drugs) into YCWPs, e.g., YGPs, and (3) the incorporation of nanoparticles with an intrinsic property, such as magnetic nanoparticles, thus increasing the versatility of the particles, as the same formulation could be used for drug delivery and the magnetic properties employed for cell purification, or imaging applications (E. Soto, et al., V. Vetvicka and M. Novak (Eds), Bentham Press, 82 pp., 2011).

The development of YCWP nanoparticle, e.g., YGP nanoparticle, loaded formulations used two types of model nanoparticles: (1) fluorescent polystyrene nanoparticles of narrow size distribution to allow for the visualization and characterization by fluorescent techniques, and (2) mesoporous silica nanoparticles (MSNs) for the encapsulation of the chemotherapeutic drug, doxorubicin to assess biological activity. MSNs are highly porous nanoparticles prepared from tetraethyl orthosilicate polymerized on a template such as a surfactant micelle (C. T. Kresge, et al., Nature, vol. 359, pp. 710-712, 1992, B. G. Trewyn, et al., Accounts of Chemical Nature, vol. 40, no. 9, pp. 846-853, 2007). Since the discovery of MSNs in 1992, research has been done to evaluate these materials for absorption, catalysis, chemical devices, and more recently as drug delivery agents (i.e., delivery of the cancer drugs camptothecin, paclitaxel, doxorubicin (E. R. Gillies, et al., Bioconjugate Chemistry, vol. 16, pp. 361-368, 2005, J. Lu, et al., Small, vol. 3, no. 8, pp. 1341-1346, 2007, J. Lu, et al., Nanobiotechnology, vol. 3, pp. 89-95, 2007)). MSNs were chosen as a model nanoparticle because of their ease of synthesis, binding capacity for small drug molecules, and the possibility of extending the capabilities of YCWP targeted, e.g., GP targeted, drug delivery to hydrophobic drugs. Delivery of doxorubicin (Dox) is studied herein as a first step in the development of YCWP/YGP macrophage targeted delivery of chemotherapeutics. Macrophages are non-dividing differentiated cells and are resistant to the cytotoxic DNA replication inhibitor, doxorubicin. Macrophages are known to migrate into solid tumors and it is believed that they will act as "Trojan horses" carrying lethal doses of Dox-GPs into tumors for targeted cancer drug delivery to rapidly dividing tumor cells.

Yeast glucan particles (YGPs) (also referred to herein as glucan particles (GPs) are featured for use in several of the nanoparticle delivery systems exemplified herein, although the skilled artisan will appreciate that other YCWPs can be readily adapted for use in the nanoparticle delivery systems of the invention. Yeast glucan particles (YGPs), or glucan particles (GPs), are porous, hollow microspheres that are prepared from Saccharomyces cerevisiae (Baker's yeast). The glucan microspheres have an average diameter of 2-4 microns and are composed of 1,3-D-Glucan and trace amounts of chitin. The 1,3-D-Glucan polysaccharide on the GP surface serves as a ligand for receptor-mediated cell uptake by phagocytic cells bearing β-glucan receptors (dectin-1 (D1) receptor and complement receptor 3 (CR3)) (G. D. Brown, et al., Nature, vol. 413, pp. 36-37, 2001), such as macrophages and dendritic cells in the immune system. GP uptake has been demonstrated to be dectin-1 dependent in vitro (H. Huang, et al., Infection and Immunity, vol. 77, pp. 1774-1781, 2009). The ability to selectively target phagocytic cells makes the glucan particle an attractive drug delivery vehicle for this cell population. The hollow and porous material properties of GPs allow for the encapsulation, transport, delivery, and release of electrostatically bound payloads. Previously, the use of GPs for macrophage-targeted delivery of a variety of soluble payload macromolecules has been described (e.g., proteins (H. Huang, et al., Infection and Immunity, vol. 77, pp. 1774-1781, 2009), DNA (E. Soto, et al., Bioconjugate Chemistry, vol. 19, no. 4, pp. 840-848, 2008) and siRNA (M. Aouadi, et al., Nature, vol. 458, pp. 1180-1184, 2009, G. Tesz, et al., Biochemical Journal, vol. 436, pp. 351-362, 2011)), and small drug molecules, such as the antibiotic Rifampicin (E. Soto, et al., Polymers, vol. 2, pp. 681-689, 2010). However, the use of GPs for small drug molecule delivery is limited since the majority of small drug molecules are neutral, monovalent in charge, or insoluble in water and such payloads are not easily trapped within glucan particles using the polyplex core or layer-by-layer (LbL) encapsulation methods developed for nucleic acids and proteins.

The present invention improves upon previously described yeast-based microencapsulation methodologies, in particular, by providing for the incorporation of nanoparticles into and/or onto yeast cell wall particles (YCWPs), for example, yeast glucan particles (microparticles) (YGPs). The improved technologies provide for delivery of nanoparticles, the nanoparticles themselves having utility in biomedical applications, or the nanoparticles imparting one or more functionalities of use in various biomedical, e.g., drug delivery applications. The present invention generally relates to loading yeast cell wall particles (YCWPs) (e.g., YGPs) with nanoparticles for receptor-targeted drug delivery. In particular, the present invention relates to loading nanoparticles either on the surface or inside the shell of a YCWP (e.g., the glucan shell of a yeast glucan particle (YGP)). The present invention further relates to methods of making a YCWP, for example, a YGP or GP, loaded with nanoparticles. The present invention also relates to methods of using the YCWPs, for example, the use of YGPs or GPs, loaded with nanoparticles for receptor-targeted delivery of the nanoparticles.

In exemplary embodiments of the invention, YCWPs, for example, YGPs or GPs, are loaded with a payload molecule, or with a nanoparticle having a functionality compatible with a payload molecule. In other exemplary embodiments, YCWPs, for example, YGPs or GPs, are loaded with a nanoparticle having a desired functionality. In certain exemplary embodiments, YCWPs, for example, YGPs or GPs, can further include a trapping molecule for trapping a payload molecule and/or a nanoparticle. In some exemplary embodiments, YCWPs, for example, YGPs or GPs, have payload molecules and/or nanoparticles loaded into the interior of the YCWP. In other exemplary embodiments, the YCWPs, for example, YGPs or GPs, have payload molecules loaded on the exterior of the YCWP.

Prior to describing the invention, it may be helpful to an understanding thereof to set forth definitions of certain terms to be used hereinafter.

As used herein, the term "microparticle" refers to a small particle or particulate system, generally larger than about one micrometer (1 μm) in diameter and can be used to describe both microcapsules and microspheres. Microparticles can be employed in a variety of drug delivery technologies and can be employed for various purposes including, but not limited to, controlled drug delivery, protection of the drugs from degradation, and protection of the body from the toxic effects of the drugs.

As used herein, the term "nanoparticle" refers to a particle having any one structural feature on a scale of less than about 1000 nm that exhibits novel properties as compared to a bulk sample of the same material. Routinely, nanoparticles have any one structural feature on a scale of less than about 100 nm. In exemplary embodiments, a nanoparticle is a particle having one or more dimensions of the order of about 1-1000 nm. In other exemplary embodiments, a nanoparticle is a particle having one or more dimensions of the order of about 1-1000 nm. A spherical nanoparticle would have a diameter, for example, of between about 1-100 or 1-1000 nanometers.

A nanoparticle most often behaves as a unit in terms of its transport and properties. It is noted that novel properties that differentiate nanoparticles from the corresponding bulk material typically develop at a size scale of under 1000 nm, or at a size of under 100 nm, but nanoparticles can be of a larger size, for example, for particles that are oblong, tubular, and the like. The size at which materials display different properties as compared to the bulk material is material-dependent and can be seen for many materials much larger in size than 100 nm and even for some materials larger in size than 1000 nm. Although the size of most molecules would fit into the above outline, individual molecules are usually not referred to as nanoparticles.

Nanoparticles are of great scientific interest as they are effectively a bridge between bulk materials and atomic or molecular structures. A bulk sample of a particular material should have constant physical properties regardless of its size, but at the nanoscale, size-dependent properties are often observed. Thus, the properties of materials change as their size approaches the nanoscale and as the percentage of atoms at the surface of a material becomes significant. For bulk materials larger than one micrometer (or micron), the percentage of atoms at the surface is insignificant in relation to the number of atoms in the bulk of the material. The interesting and sometimes unexpected properties of nanoparticles are therefore largely due to the large surface area of the material, which dominates the contributions made by the small bulk of the material.

As used herein, the term "yeast cell wall particle" ("YCWP") refers to a particle (e.g., a microparticle) derived from a yeast cell, i.e., a naturally-occurring yeast cell, having at least one component of the yeast cell wall modified, e.g., extracted. An exemplary yeast cell is *Saccharomyces cerevisiae*. *S. cerevisiae* cell walls comprise components including, but not limited to, glucan, chitosan, mannan, proteins and the like. Extraction of one or more of these components from a naturally occurring yeast cell wall results in a YCWP. Exemplary YCWP include yeast glucan particles (YGPs) (or GPs), yeast chitosan particles (YCPs), and yeast chitosan/mannan particles (YCMPs), as describes in detail infra. Based on their size, YCWPs can also be referred to herein and in the art as microparticles. As used herein, a YCWP is typically a yeast cell wall particle of 80-85% beta glucan purity.

As used herein, the term "load" refers to the introduction or insertion of a substance or object (e.g., a payload or nanoparticle) into or onto a particle of the invention, for example, a YCWP, at a desired location. As used herein, the term "loading" refers to introducing or inserting a substance or object (e.g., a payload or nanoparticle) into or onto a particle of the invention, for example, a YCWP, at a desired location. "Loading" can further include "trapping" or covalently linking the nanoparticles with the YCWP, YGP, or GP. In preferred embodiments of the invention, loading also includes trapped or linking the substance or object at the desired location, for example in a core or on the surface of onto a particle of the invention, for example, a YCWP.

As used herein, the term "payload" refers to a substance, e.g., a small molecule or biomolecule (e.g., protein, peptide, nucleic acid, etc.) to be loaded (or loaded) into a YCWP of the invention, either alone, or in combination, or conjunction with, a nanoparticle of the invention.

By "protein" is meant a sequence of amino acids for which the chain length is sufficient to produce the higher levels of tertiary and/or quaternary structure. This is to distinguish from "peptides" or other small molecular weight drugs that do not have such structure. Typically, the protein herein will have a molecular weight of at least about 15-20 kD, preferably at least about 20 kD.

"Essentially pure" means a composition comprising at least about 90% by weight of the desired molecule, based on total weight of the composition, preferably at least about 95% by weight. "Essentially homogeneous" means a composition comprising at least about 99% by weight of the desired molecule, based on total weight of the composition.

By "nucleic acid" is meant a biopolymers comprised of constituent monomers, ribo- or deoxyribonucleotides, or analogs thereof. "Nucleic acids" include naturally-occurring polynucleotides, for example, DNA, RNA, etc. Synthetic nucleic acids are also exemplary "payloads" including, for example, antisense nucleic acids, siRNA, and the like.

By "small molecule" is meant a low molecular weight organic compound which is by definition not a polymer. The upper molecular weight limit for a small molecule is approximately 800 Daltons which allows for diffusion across cell membranes, e.g., mammalian cell membranes. Small molecules can have a variety of biological functions, e.g., cell signaling molecules, drugs, pesticides (in agriculture), etc. The compounds can be natural or artificial. Very small oligomers can also be considered "small molecules", such as dinucleotides, peptides and disaccharides.

The term "drug" refers to a substance that, when absorbed into the body of a living organism, alters normal bodily function.

The term "patient" includes human and other mammalian subjects that receive either prophylactic or therapeutic treatment.

The term "effective dose" or "effective dosage" is defined as an amount sufficient to achieve or at least partially achieve the desired effect. The term "therapeutically effective dose" is defined as an amount sufficient to cure or at least partially arrest a disease and/or its complications in a patient already suffering from the disease.

The invention features YCWPs, for example, YGPs or GPs, loaded with payload molecules or loaded with payload molecules and nanoparticles having desired functionalities. The following sections provide detailed descriptions of methods of making and using exemplary YCWPs of the invention.

I. Methods of Making Yeast Cell Wall Particles (YCWPs)

YCWPs exhibit key functional properties of the native or naturally-occurring yeast from which they are derived. Extracted yeast cell wall particles, primarily due to their beta-glucan content, are targeted to phagocytic cells, such as macrophages and cells of lymphoid tissue. The mucosal-associated lymphoid tissue (MAT) comprises all lymphoid cells in epithelia and in the lamina propria lying below the body's mucosal surfaces. The main sites of mucosal-associated lymphoid tissues are the gut-associated lymphoid tissues (GALT), the bronchial-associated lymphoid tissues (BALT), and the SALT skin-associated lymphoid tissue (SALT).

Another important component of the GI immune system is the M or microfold cell. M cells are a specific cell-type in the intestinal epithelium over lymphoid follicles that endocytose a variety of protein and peptide antigens. Instead of digesting these proteins, M cells transport them into the underlying tissue, where they are taken up by local dendritic cells and macrophages. M cells are another target of YCWPs on the invention. M cells take up molecules and particles from the gut lumen by endocytosis or phagocytosis. This material is then transported through the interior of the cell in vesicles to the basal cell membrane, where it is released into the extracellular space. This process is known as transcytosis and has been shown to occur effectively for uptake of YCWPs (see e.g., Beier and Gebert, Am J. Physiol. 1998 July; 275 (1 Pt 1):G130-7 and van der Lubben, et al., J Drug Target, 2002 September; 10 (6):449-56. Without being bound in theory, it is believed that uptake of YCWPs into cells, for example macrophage cells, occurs at least in part due to specific receptor-mediated uptake. For example, it is known that pathogen pattern recognition receptors (PRRs) recognize common structural and molecular motifs present on microbial surfaces and that mannose receptors and beta-glucan receptors, in part, participate in the recognition of fungal pathogens.

The mannose receptor (MR), a carbohydrate-binding receptor expressed on subsets of macrophages, is considered one such PRR. Macrophages have receptors for both mannose and mannose-6-phosphate that can bind to and internalize molecules displaying these sugars. The molecules are internalized by endocytosis into a pre-lysosomal phagosome. This internalization has been used to enhance entry of oligonucleotides into macrophages using bovine serum albumin modified with mannose-6-phosphate and linked to an oligodeoxynucleotide by a disulfide bridge to a modified 3' end. See, e.g., Bonfils, et al., Nucl. Acids Res. 1992 20, 4621-4629; and Bonfils, et al., Bioconj. Chem., 3, 277-284 (1992).

Macrophages also express beta-glucan receptors, including complement receptor 3 (CR3) (Ross, et al., 1987, Complement Inflamm. 4:61), dectin-1. (Brown and Gordon. 2001. Nature 413:36), and lactosylceramide (Zimmerman et al., J Biol. Chem. 1998 Aug. 21:273 (34):22014-20). The beta-glucan receptor, CR3 is predominantly expressed on monocytes, neutrophils and NK cells, whereas dectin-1 is predominantly expressed on the surface of cells of the macrophages. Lactosylceramide is found at high levels in M cells. Microglia can also express a beta-glucan receptor (Muller, et al., Res Immunol. 1994 May; 145 (4):267-75). There is evidence for additive effects on phagocytosis of binding to both mannose and beta-glucan receptors. (Giaimis, J., et al., J Leukoc Biol. 1993 December; 54 (6):564-71).

In some embodiments, hollow beta 1,3-D-glucan microsphere-based delivery system incorporating payloads as polymer complexes can be used. The payload molecules can include for example, plasmid/mRNA molecules, protein molecules, nanoparticles, siRNA/oligonucleotides, up to 200% w/w small molecules. In certain embodiments, a multiplexed co-delivery of different payloads is possible. In various embodiments, beta glucan receptor-mediated uptake by antigen presenting cells can be performed. The methods of the invention can be utilized for delivering payload(s) to dendritic cells, macrophages and tissues containing these cells.

Exemplary extracted yeast cell wall particles (YCWPs) are readily available, biodegradable, substantially spherical particles about 2-4 um in diameter. Preparation of extracted yeast cell wall particles is known in the art, and is described, for example in U.S. Pat. Nos. 4,992,540, 5,082,936, 5,028,703, 5,032,401, 5,322,841, 5,401,727, 5,504,079, 5,968,811, 6,444,448 B1, 6,476,003 B1, published U.S. applications 2003/0216346 A1, 2004/0014715 A1, and PCT published application WO 02/12348 A2.

A form of extracted yeast cell wall particles, referred to as "whole glucan particles" (WGPs), have been described in the art and suggested as delivery vehicles of, for example, small molecules and other payload molecules. The use of WGPs, alone as delivery vehicles, however, is limited either to release by simple diffusion of active ingredient from the particle or release of an agent chemically cross-linked to the whole glucan particle by biodegradation of the particle matrix. See U.S. Pat. Nos. 5,032,401 and 5,607,677. Accordingly, a key feature of the invention lies in the modification of WGP methodologies to facilitate improved retention and/or delivery of payload molecules. Such improvements build on the art-recognized WGPs but feature trapping molecules and nanoparticles as well as pluralities of said trapping molecules and nanoparticles, formulated in specific forms to achieve the desired improved delivery properties. As used herein, a WGP is typically a whole glucan particle of >90% beta glucan purity.

A. Preparation of Glucan Particles

Glucan particles (GPs), also referred to herein as yeast glucan particles ("YGPs"), are a purified hollow yeast cell 'ghost' containing rich β-glucan sphere, generally 2-4 microns in diameter. In general, glucan particles can be prepared from yeast cells by the extraction and purification of the alkali-insoluble glucan fraction from the yeast cell walls. The yeast cells can be treated with an aqueous hydroxide solution without disrupting the yeast cell walls, which digests the protein and intracellular portion of the cell, leaving the glucan wall component devoid of significant protein contamination, and having substantially the unaltered cell wall structure of β(1-6) and β(1-3) linked glucans. The 1,3-β-glucan outer shell provides for receptor-mediated uptake by phagocytic cells expressing β-glucan receptors.

Certain glucan particles, can be made as follows: Yeast cells (*S. cerevisae* strain R4) can be grown to midlog phase in minimal media under fed batch fermentation conditions. Cells can be harvested by batch centrifugation for example, at about 2000 rpm for about 10 minutes. The cells can be then washed once in distilled water and then re-suspended in 1 liter of 1M NaOH and heated to 90 degrees Celsius. The cell suspension can be stirred vigorously for 1 hour at this temperature. The insoluble material, containing the cell walls, can be recovered by centrifuging. This material can be then suspended in 1M NaOH and heated. The suspension can be stirred vigorously for 1 hour at this temperature. The suspension can be then allowed to cool to room temperature and the extraction can be continued for a further 16 hours. The insoluble residue can be recovered by centrifugation. This material can be finally extracted in water brought to pH 4.5 with HCl. The insoluble residue can be recovered by centrifugation and washed three times with water, isopropanol and acetone. The resulting slurry can be placed in glass trays and dried under reduced pressure to produce a fine white powder.

A more detailed description of processes for preparing the above particles can be found in U.S. Pats. Nos. 4,810,646; 4,992,540; 5,028,703; 5,607,677 and 5,741,495, the teachings of which are incorporated herein by reference. For example, U.S. Pat. No. 5,028,703 discloses that yeast WGP particles can be produced from yeast cells in fermentation culture. The cells can be harvested by batch centrifugation at 8000 rpm for 20 minutes in a Sorval RC2-B centrifuge. The cells can be then washed twice in distilled water in order to prepare them for the extraction of the whole glucan. The first step involved resuspending the cell mass in 1 liter 4% w/v NaOH and heating to 100 degrees Celsius. The cell suspension can be stirred vigorously for 1 hour at this temperature. The insoluble material containing the cell walls can be recovered by centrifuging at 2000 rpm for 15 minutes. This material can be then suspended in 2 liters, 3% w/v NaOH and heated to 75 degrees Celsius. The suspension can be stirred vigorously for 3 hours at this temperature. The suspension can be then allowed to cool to room temperature and the extraction can be continued for a further 16 hours. The insoluble residue can be recovered by centrifugation at 2000 rpm for 15 minutes. This material can be finally extracted in 2 liters, 3% w/v NaOH brought to pH 4.5 with HCl, at 75 degrees Celsius for 1 hour. The insoluble residue can be recovered by centrifugation and washed three times with 200 milliliters water, once with 200 milliliters dehydrated ethanol and twice with 200 milliliters dehydrated ethyl ether. The resulting slurry can be placed on petri plates and dried.

Varying degrees of purity of glucan particles can be achieved by modifying the extraction/purification process. As used herein, the terms YCWP, YGP, and GP describe a 2-4 micron hollow microsphere (or yeast cell wall ghost) purified from Baker's yeast using a series of alkaline, acid and organic extraction steps as detailed supra. In general, these GPs are on the order of 80-85% pure on a w/w basis beta glucan and, following the introduction of payload, trapping and other components, become of a slightly lesser "purity". In exemplary embodiments, GPs are <90% beta glucan purity.

GPs have been used for macrophage-targeted delivery of soluble payloads (DNA, siRNA, protein, small molecules) encapsulated inside the hollow GPs via core polyplex and layer-by-layer (LbL) synthetic strategies.

B. Preparation of YCP Particles

Yeast cells (*Rhodotorula* sp.) derived from cultures obtained from the American Type Culture Collection (ATCC, Manassas, Va.) can be aerobically grown to stationary phase in YPD at 30 degrees Celsius. *Rhodotorula* sp. cultures available from ATCC include Nos. 886, 917, 9336, 18101, 20254, 20837 and 28983. Cells can be harvested by batch centrifugation at 2000 rpm for 10 minutes. The cells can be then washed once in distilled water and then re-suspended in water brought to pH 4.5 with HCl, at 75 degrees Celsius for 1 hour. The insoluble material containing the cell walls can be recovered by centrifuging. This material can be then suspended in 1 liter, 1M NaOH and heated to 90 degrees Celsius for 1 hour. The suspension can be then allowed to cool to room temperature and the extraction can be continued for a further 16 hours. The insoluble residue can be recovered by centrifugation and washed twice with water, isopropanol and acetone. The resulting slurry can be placed in glass trays and dried at room temperature to produce 2.7 g of a fine light brown powder.

In alternative embodiments, YGPs, e.g., activated YGPs, can be grafted with chitosan on the surface, for example, to increase total surface chitosan. Chitosan can further be acetylated to form chitin, in certain embodiments (YGCP). Such particles can be seen to have equivalent properties when seen, in vivo, by the immune system of a subject or patient.

C. Preparation of YGMP Particles

*S. cerevisiae* (100 g Fleishmans Bakers yeast) can be suspended in 1 liter 1M NaOH and heated to 55 degrees Celsius. The cell suspension can be mixed for 1 hour at this temperature. The insoluble material containing the cell walls can be recovered by centrifuging at 2000 rpm for 10 minutes. This material can be then suspended in 1 liter of water and brought to pH 4-5 with HCl, and incubated at 55 degrees Celsius for 1 hour. The insoluble residue can be recovered by centrifugation and washed once with 1000 milliliters water, four times with 200 milliliters dehydrated isopropanol and twice with 200 milliliters acetone. The resulting slurry can be placed in a glass tray and dried at room temperature to produce 12.4 g of a fine, slightly off-white, powder.

*S. cerevisiae* (75 g SAF-Mannan) can be suspended in 1 liter water and adjusted to pH 12-12.5 with 1M NaOH and heated to 55 degrees Celsius. The cell suspension can be mixed for 1 hour at this temperature. The insoluble material containing the cell walls can be recovered by centrifuging at 2000 rpm for 10 minutes. This material can be then suspended in 1 liter of water and brought to pH 4-5 with HCl, and incubated at 55 degrees Celsius for 1 hour. The insoluble residue can be recovered by centrifugation and washed once with water, dehydrated isopropanol and acetone. The resulting slurry can be placed in a glass tray and dried at room temperature to produce 15.6 g of a fine slightly off-white powder.

II. Payload Molecules and Nanoparticles

The particulate delivery system of the present invention is useful for in vivo or in vitro delivery of payload molecules, optionally, in combination or associated with complementary nanoparticles. Exemplary payload molecules include, but are not limited to, nucleic acids, proteins, peptides and enzymes. In addition to nucleic acids, proteins and peptides, the particulate delivery system of the present invention is suitable for the delivery of smaller molecules, preferably for the delivery of pharmaceutically active agent, more preferably therapeutic small molecules.

Preparations of payload molecules are preferably essentially pure and desirably essentially homogeneous (i.e., free from contaminating molecules, etc). Exemplary nanoparticles include, but are not limited to such as fluorescent styrenes, non-fluorescent styrenes, quantum dots, paramagnetic and/or ferromagnetic particles such as iron oxides, and gold nanoparticles. Nanoparticles other than the above examples can be used in the present invention as long the GPs can be effectively loaded with the nanoparticles using the methods described vide infra.

Other exemplary nanoparticles include, but are not limited to, plastic, glass, silicon, polymeric (e.g., PGLA), ceramic, oxides, metal and other particles, labeled, unlabeled, functionalized and the like. Essentially nanoparticles of any composition can be contemplated for use in the invention, given that they either meet the size restriction to load them inside the particles of the invention, or contain a chemical handle to either absorb or chemically link larger nanoparticles to the outer surface particles of the invention.

III. Payload Trapping Molecules

Exemplary embodiments of the invention feature payload molecules and/or nanoparticles, optionally in combination or associated with complementary trapping molecules, to facilitate one or more desired delivery properties (e.g., sustained release, protection of payload, etc.) The payload trapping molecule is preferably a pharmaceutically acceptable molecule. The payload and trapping molecule can be both soluble in the solvent system; the solvent system can be absorbed through the yeast cell particle carbohydrate matrix allowing the absorption of the payload and trapping polymer. The payload and trapping molecule can be water soluble. In preferred embodiments, the trapping molecule is biodegradable.

The mechanism of action of the trapping reaction with a given payload dictates the choice of payload trapping molecule. For electrostatic interactions a charged payload trapping molecule of opposite charge of the payload is required. For physical entrapment, the payload trapping molecule suitably participates in the formation of a matrix that reduces the diffusion of a payload. In other embodiments, the payload trapping molecule contributes a hydrophobic binding property that contributes to the retention of the payload. In further embodiments, the payload trapping molecule selectively binds to the payload, providing an affinity interaction that contributes to the retention of the payload.

In general, polyelectrolytes can be suitable payload trapping molecules. Several suitable polyelectrolytes are disclosed in U.S. Pat. Nos. 7,740,861 and 6,133,229 and are herein incorporated by reference in their entirety. The polyelectrolyte may be a cationic or anionic polyelectrolyte. Amphoteric polyelectrolytes may also be employed. The cationic polyelectrolyte is preferably a polymer with cationic groups distributed along the molecular chain. The cationic groups, which in certain embodiments may include quaternary ammonium-derived moieties, may be disposed in side groups pendant from the chain or may be incorporated in it. Examples of cationic polyelectrolytes include: substituted polyacrylamides; polyethyleneimine, polypropyleneimine and substituted derivatives; polyamine homopolymers; polyamine co-polymers (e.g., condensates of epichlorohydrin and mono or dimethylamine); polydiallyl dimethyl ammonium chloride; substituted dextrans; modified guar gum (substituted with hydroxypropytrimonium chloride); substituted proteins (e.g., quaternary groups substituted on soya protein and hydrolysed collagen); polyamino acids (e.g., polylysine); low molecular weight polyamino compounds (e.g., spermine and spermidine) and cationic proteins, such as protamine. Natural or artificial polymers may be employed. Cationic polyelectrolytes with MW 150 to 5,000,000, preferably 5000 to 500,000, more preferably 5000 to 100,000 may be employed. An amount of 0.01 to 10% is preferred, more preferably 0.1 to 2% w/v, especially 0.05 to 5%.

The anionic polyelectrolyte is preferably a polymer with anionic groups distributed along the molecular chain. The anionic groups, which may include carboxylate, sulfonate, sulphate or other negatively charged ionisable groupings, may be displayed upon groups pendant from the chain or bonded directly to the polymer backbone. Natural or artificial polymers may be employed.

Examples of anionic polyelectrolytes include: a copolymer of methyl vinyl ether and maleic anhydride, a copolymer of methyl vinyl ether and maleic acid, alginic acid and salts; carboxymethyl celluloses and salts; substituted polyacrylamides (eg substituted with carboxylic acid groups); polyacrylic acids and salts; polystyrene sulfonic acids and salts; dextran sulphates; substituted saccharides e.g., sucrose octosulfate; heparin. Anionic polyelectrolytes with MW of 150 to 5,000,000 may be used, preferably 5000 to 500,000, more preferably 5000 to 100,000. An amount of 0.01% to 10% is preferred especially 0.05 to 5% more especially 0.1 to 2% w/v.

Biological polymers, such as polysaccharides, are preferred trapping polymers. Preferably, the polymers are processed to an average molecular weight to less than 100,000 Daltons. The polymers are preferably derivatized to provide cationic or anionic characteristics. Suitable polysaccharides include chitosan (deacetylated chitin), alginates, dextrans, such as 2-(diethylamino) ethyl ether dextran (DEAE-dextran) and dextran sulphate, xanthans, locust bean gums and guar gums.

Cationic lipids are also known in the art to be suitable for transfection. Suitable cationic lipids include N-[1-(2,3-dioleyloxy)propyl]-N,N,N-trimethylammonium chloride (DOTMA), [N,N,N,N'-tetramethyl-N,N'-bis(2-hydroxyethyl)-2,3-di(oleoyloxy)-1,4-butanediammonium iodide], dioctadecylamidoglycyl spermine, N-[1-(2,3-Dioleoyloxy)]-N,N,N-trimethylammonium propane methylsulfate (DOTAP), N-[1-(2,3-dioleyloxy)propyl]-N,N,N-trimethylammonium chloride, 1,2-dimyristyloxypropyl-3-dimethylhydroxy ethyl ammonium bromide (DMRIE), dimyristoleoyl phosphonomethyl trimethyl ammonium (DMPTA), 1,2-dioleoyl-sn-glycero-3-phosphoethanolamine-N-(7-nitro-2-1,3-benzoxadia-zol-4-yl), ammonium salt, 1,2-dioleoyl-3-trimethylammonium-propane chloride, 1,2-dioleoyl-sn-glycero-3-phosphoethanolamine and 1,3-dioleoyloxy-2-(6-carboxyspermyl)propylamide (DOSPER).

IV. Loading Components into Yeast Cell Wall Particles, e.g., Yeast Glucan Particles The invention features nanoparticles, optionally in combination or associated with payload molecules, obtained, in exemplary embodiments by loading the nanoparticles and/or payload molecules into or onto the YCWPs, e.g., YGPs. As used herein, a YGP is typically a yeast glucan particle of 80-85% beta glucan purity.

A. Loading Soluble Components

A variety of methods of loading payload molecules and/or payload trapping molecules glucan particles are described in detail in U.S. Pat. No. 7,740,861 and U.S. application Ser. No. 12/260,998, published as US 20090226528, the contents of which are herein incorporated by reference in their entirety. In some embodiments, both, the payload molecule as well as the payload trapping molecule are soluble in the same solvent. In certain embodiments the solvent can be water or an organic solvent. In various embodiments, the solvent is water.

B. Polyplexed Payloads

Polyplexed payloads encapsulated inside the glucan particles can be prepared by first introducing payload molecules into the glucan particle to form a core. In some embodiments, the core can be made of nucleic acids such as DNA or RNA, proteins or peptides, natural or synthetic molecules and/or polymers, inorganic complexes and other synthetic, organic, inorganic or biological particles. The payload molecules can then be coated with a payload trapping molecule to result in a polyplexed payload. In some embodiments, the payload trapping molecule is a polymer. In certain embodiments, the payload trapping molecule is oppositely charged than the payload molecule. For example, if the payload molecule is a nucleic acid, the core is anionic. The anionic core can be coated with a cationic polymer as a payload trapping molecule to form the resulting polyplexed payload encapsulated inside the glucan particle. A variety of methods of making polyplexed payloads encapsulated by a glucan particle are described in detail in U.S. Pat. No. 7,740,861 and in "Characterization of Multilayered Nanoparticles Encapsulated in Yeast Cell Wall Particles for DNA Delivery" by Ernesto R. Soto and Gary R. Ostroff. *Bioconjugate Chem.,* 2008, 19 (4), pp 840-848, the contents of which are herein incorporated by reference in their entirety.

Advantages of polyplexed payloads include: large payload capacity, ease of synthesis of multiplexed core/layered formulations containing macromolecules (i.e. DNA, siRNA, proteins) held together via non-covalent interactions with trapping polymers, and controlled release in which the outermost payload layers release first.

C. Layer by Layer Synthesis of Payloads in GP

A variety of methods of layer-by-layer synthesis of payloads in GP are described in detail in application Ser. No. 12/260,998, published as US 20090226528, the contents of which are herein incorporated by reference in their entirety. As used herein, a GP is typically a glucan particle derived from yeast of 80-85% beta glucan purity.

GPs can be developed using layer by layer (LbL) self-assembly of nanomaterials held together by electrostatic interactions in order to provide nanoparticulate materials that protect and deliver payload molecules to cells. Exemplary payload molecules are nucleic acid-based payload molecules and include, but are not limited to DNA molecules, e.g., vectors, cassettes, etc., RNA molecules, e.g, RNA molecules encoding proteins, miRNAs, siRNAs, hairpin RNAs, anti-sense RNAs, etc., ribozymes, and the like. The payload agent delivery technology can be based on the in situ layer by layer synthesis of nanoparticles caged within hollow yeast cell wall particles (YCWP). YCWP provide protection and facilitate oral and systemic receptor-targeted delivery of payload molecules to phagocytic cells.

In particular embodiments, yeast cell wall particles can be an effective material to encapsulate payloads following layer-by-layer assembly of polymers by electrostatic interactions caged inside hollow YCWP. Labeling of each layer with fluorescent molecules, such as rhodamine fluorescein, Cy3, and the like, can allow quantitative fluorescence analysis and optimization of LbL nanoplex formation within YCWP.

YCWP are porous hollow 2-4 micron microspheres prepared from Baker's yeast composed primarily of beta 1,3-D-glucan, mannoproteins and chitin. Nanoparticulate cores composed of anionic and cationic polymers can be constructed from tRNA and PEI within YCP. These YCWP encapsulated cationic nanoparticulate cores can be used to absorb payloads onto the nanoparticulate surface and then coated with PEI.

Rhodamine labeled tRNA, DNA (or siRNA) or PEI can be used for optimization of the formation of each layer of the encapsulated nanoparticles. A calibration curve for each labeled compound can be used for quantitative binding.

The nanoparticles inside YCWP can consist of a core of tRNA/polyethylenimine (PEI) followed by a DNA layer that is finally coated with a protective layer of PEI. Using rhodamine labeling of tRNA, PEI and DNA, the layer-by-layer formation of the nanoparticles can be visualized by fluorescent microscopy and quantified by fluorescence spectroscopy and flow cytometry. Embodiments as above, wherein the components are unlabeled are also clearly within the scope of the invention.

D. YCWP Loading

The YCWPs (e.g., glucan particles) can be loaded with nanoparticles in several different ways. In some embodiments, the nanoparticles can be installed on the outer surface of the YCWPs (e.g., glucan particles). In certain embodiments, the nanoparticles can be encapsulated within the YCWPs (e.g., glucan particles) such that they are embedded within the matrix of the YCWPs (e.g., glucan particles). In various embodiments, the nanoparticles can be encapsulated within the YCWPs (e.g., glucan particles) such that they are embedded within the inner cavity of the hollow YCWPs (e.g., glucan particles).

An advantage of loading the nanoparticles on the outer surface is that nanoparticles of a size greater than 40 nm can be effectively installed on the shell of the YCWPs (e.g., glucan particles) and delivered to a target site using glucan mediated delivery.

A variety of linkers can be used to load the nanoparticles on the outer surface of the YCWPs (e.g., glucan particles). Different nanoparticles can be installed at different anatomical locations of the YCWPs (e.g., glucan particles). In some embodiments, the linker can be attached or detached from the nanoparticles and/or the YCWPs (e.g., glucan particles) via a reversible cross-linking chemical reaction. In various embodiments, the linker can be attached or detached from the nanoparticles and/or the YCWPs (e.g., glucan particles) via a change in the pH, a change in the redox potential, hydrolysis, or by enzymatic methods. A skilled artisan appreciates the various methods that are available for such a reversible cross-linking of groups. In certain embodiments, the linker can be a disulfide, acetal, ketal, orthoester, or an ester group. In various embodiments, the linker can be a peptide moiety.

Once the YCWPs (e.g., glucan particles) have delivered the nanoparticles installed on the outer shell to the target site, the linkage of the nanoparticles to the outer YCWPs (e.g., glucan particles) can be broken, for example due to hydrolysis. In some embodiments, the linkage can be broken as a result of phagocytosis of the outer YCWP shell. Once the linkage of the nanoparticles to the outer YCWP shell is broken, the free form of the nanoparticles can be delivered at the target site as desired.

In some embodiments, the YCWPs (e.g., glucan particles) can be treated with oxidizing agents such as periodate followed by Schiff base formation with amines such as biotin-$NH_2$, cyclodextrin-$NH_2$, protein/peptide, alkylamines, polyamines, amino carboxylates/phosphates/sulfates, and alkyne-$NH_2$. A reduction of the Schiff base using reducing agents such as sodium borohydride can result in surface loading of the various payload molecules such as biotin, cyclodextrins, proteins, alkynes, and aminocarboxylates.

E. Nanoparticle Loading of YCWPs (e.g., YGPs or Glucan Particles)

FIG. 1 shows an exemplary schemes describing the nanoparticle loading strategy inside (or on the surface of) a YCWP, namely a YGP of the invention. In some embodiments, the nanoparticles can be installed or encapsulated within the YCWPs, e.g., YGPs or GPS (also referred to herein as glucan shells). A "pull-push" mechanism can be employed to effectively encapsulate the nanoparticles either just inside the particle, e.g., shell such that the nanoparticles are embedded in the matrix, or all the way into the inner cavity of the particle, e.g., the hollow glucan shell. The "pull-push" mechanism can comprise capillary diffusion action "pulling" the nanoparticles through the particle matrix, e.g., the glucan shell matrix and following, a drying step by, for example, lyophilization, the dry particle, e.g., dry glucan glucan particle, can be rehydrated to "push" the nanoparticle cargo inside the particle. The concept of "pull-push" vs. "pull and push" can describe the same action.

When loading payloads (including NP payloads), loading can be performed using "sub-hydrodynamic" volumes. The phrase "sub-hydrodynamic" volume can be used to characterize the aqueous absorption volume of the YCWPs (e.g., YGPs or GPs.) Typically YCWPs (e.g., YGPs) can absorb 10 times their weight in water (or solvent, e.g., aqueous solvent.) In some embodiments, water (or solvent, e.g., aqueous solvent) that is in an amount 5 times the weight of the YCWP (e.g., YGP) can be used as a "sub-hydrodynamic" volume to load a payload into YCWPs (e.g., YGPs.) The loading can result in a uniformly wet paste of particles containing payload. In certain embodiments, a sub-hydrodynamic volume is about 50% of the maximum aqueous absorption volume of the YCWPs. In certain embodiments, the sub-hydrodynamic volume is about 10-50% (i.e., about 10, 20, 30, 40 or 50%) of the maximum aqueous absorption volume of the YCWPs. In other embodiments, the sub-hydrodynamic volume is about 50-90% (i.e., about 50, 60, 70, 80 or 90%) of the maximum aqueous absorption volume of the YCWPs. The skilled artisan will appreciate that altering the sub-hydronamic loading volume will result in suspensions (e.g., pastes) that are more or less wet in nature, the latter of which may facilitate loading.

An advantage of this method is that if a payload (e.g., NP) is outside the YCWP, e.g., glucan particle shell, when a trapping polymer is added, then the reaction between the payload and the trapping polymer can also occur outside the YCP, e.g., glucan shell, and in effect that material is not encapsulated. Typically, when performing a first (e.g., primary) sub-hydrodynamic volume loading reaction >85% of the payload can be absorbed, or "pulled" inside the glucan shell boundary by capillary action and the payload can be encapsulated upon addition of trapping polymer.

This phenomenon can leave up to about 15% of the payload outside. To reduce the amount of payload (e.g., NP) outside the YCWP, e.g., GP shell, the particles loaded with payload can be dried, for example, by lyophilization, spray drying, etc. The sub-hydrodynamic volume loading reaction step can be repeated with solvent (e.g., aqueous solvent, for example, buffer or water) only. Upon addition of solvent the payload outside the shells can be re-dissolved and swept inside the particles or shells by capillary action as the particles/shells (YCWPs, e.g., YGPs) rehydrate.

This phenomenon can be referred to as a "push" reaction as it not only pulls the payload inside by capillary action as in the primary loading reaction, but it pushes in any payload that is in the boundary of the glucan shell itself into the internal hollow cavity of the particle. As a result about >85% of the remaining material outside can now be loaded inside the GP yielding about <5% of payload outside in the final product. If necessary this push (e.g., water push) can be repeated additional times, e.g., one, two, three or more times) to get cleaner formulations.

In some embodiments, the hydration/drying series of steps can be performed in sequential steps (hydration-lyophilization-hydration). In certain embodiments, the sequential process can be performed as a continuous process. In various embodiments, the steps can be performed by spray drying, or using fluidized bed drying.

In some embodiments, 2-20 nm nanoparticles can be loaded into the glucan particles with greater than 40% loading. In certain embodiments, 10-40 nm (e.g., 21-40 nm) nanoparticles can be loaded into the glucan particles with about 30-40% loading. In various embodiments, nanoparticles with a size greater than 40 nm can be loaded into the glucan particles with less than about 30% loading.

In some embodiments, fluorescent red nanoparticles can be loaded. In certain embodiments, fluorescent green nanoparticles can be loaded. In various embodiments, both red and green nanoparticles can be loaded simultaneously into the glucan particle. In certain embodiments, different species of nanoparticles can be simultaneously delivered to the target site.

Suspensions of YCWPs and NPs can include, in exemplary embodiments, NPs at a concentration of $1-10\times10^{15}$ particles/ml, e.g., at a concentration of about $5\times10^{15}$ particles/ml, mixed, for example, with dry YCWPs, (e.g., YGPs) at ratios of 1 mg/50 suspension. Exemplary ratios of YCWPs to NP suspension (w/v) include, for example, 0.1 to 0.5 mg/µl, e.g., 0.2 mg YCWP/µl NP suspension.

Exemplary suspensions, e.g., NP suspensions can be made in aqueous solvents, e.g., buffers, saline solutions or water. Exemplary sterilization can made in alcohol, e.g., ethanol solutions.

F. Experimental Procedures

In some embodiments, the nanoparticles can be loaded by modifying the pore size of the YCWP matrix. In certain embodiments, the YCWPs (e.g., glucan particles) can be treated with dimethyl sulfoxide or a urea solution, such that some of the fibers of the YCWP shell are solubilized thereby causing a thinning out of the shell wall matrix. In various embodiments, the YCWPs (e.g., glucan particles) can be treated with enzymes such as for example, zymolase. Enzymatic digestion of the YCWPs (e.g., glucan particles) can cause partial degradation of the YCWP shell causing the removal of some of the fibers leading to the increase in the pore size of the YCWP matrix.

In certain embodiments, the YCWPs (e.g., glucan particles) can be subjected to a high temperature in presence of diluted acids such as hydrochloric acid or acetic acid at a pH of about 3-4 in an autoclave. Such treatment can hydrolyze some of the glucan bonds causing an increase in the pore size of the YCWP (e.g., glucan particle) matrix.

In some embodiments, the YCWPs (e.g., glucan particles) can be treated with nitrous acid. Such a treatment can cause hydrolysis of the chitin in the cell wall, thereby reducing the extent of cross-linking, making the particles more easily/readily extractable and causing an increase in the pore size of the YCWP matrix.

G. Polymeric Nanoparticles

A variety of polymeric nanoparticles can be loaded onto/into the YCWPs (e.g., glucan particles) and effectively delivered to the target. In some embodiments, labeled, e.g., fluorescently-labeled, nanoparticles can be delivered. In certain embodiments, commercially available polymeric nanoparticles can be delivered. In various embodiments, the polymeric nanoparticles can be about 10-100 nm in size. More preferably, the polymeric nanoparticles can be about 20-40 nm in size. As a proof-of concept, polystyrene nanoparticles of various sizes were loaded into GPs to exemplify GP-NPs of the invention.

Carboxylate modified fluorescent polystyrene nanoparticles of 20 and 40 nm (Invitrogen) were loaded inside the glucan particles using the pull-push mechanism and trapped inside the glucan particles using payload trapping molecules such as cationic polymers, e.g., polyethylene imine (PEI).

The carboxylic acid groups allow for electrostatic binding with cationic polymers or covalent linkage of proteins or other polymeric materials via EDAC crosslinking. 1-Ethyl-3-[3-dimethylaminopropyl]carbodiimide hydrochloride (EDC or EDAC) is a zero-length crosslinking agent used to couple carboxyl groups to primary amines. EDAC is a water-soluble carbodiimide crosslinker that activates carboxyl groups for spontaneous reaction with primary amines, enabling peptide immobilization and hapten-carrier protein conjugation.

A variety of methods are available to a skilled artisan to detect the loading of nanoparticles into the YCWPs, e.g., glucan particles, and monitor the extent of their uptake into cells. Light-phase, contrast, or fluorescent microscopy, for example, can be used to detect the loading of nanoparticles into the YCWPs, e.g., glucan particles, and monitor the extent of their uptake into cells. Using fluorescent microscopy, visualization of glucan particles loaded with either 20 nm or 40 nm carboxylate modified fluorescent polystyrene nanoparticles was possible, and their uptake into cells (i.e., 3T3-D1 cells) was readily observable. The 40 nm particles were loaded into GPs at low yield. Only a few of the GPs in each sample contained NPs. (These samples were not evaluated for cell uptake.)

Empty GP shells can be taken in tubes followed by adding saline solution and fluorescent polystyrene nanoparticles. Incubation, centrifugation and washing can result in encapsulation of the nanoparticles and removal of the unbound particles. The fluorescence of unbound fluorescent polystyrene nanoparticles can be measured. The samples can be resuspended in saline solution and the fluorescence of bound fluorescent polystyrene nanoparticles can also be measured. Therefore, the amount of fluorescent polystyrene nanoparticles encapsulated in the GP shells can be measured.

These results show proof of concept that up to 40 nm nanoparticles, can be loaded into GP shells by numerous trapping strategies. These results show, in particular, that up to 30 nm nanoparticles, can be loaded quite efficiently into GP shells by the trapping strategies described herein.

H. Quantum Dots

As a second proof-of-concept experiment, GPs were loaded with nanoparticles such as for example, quantum dots. Quantum dots are minuscule crystals of semiconductor material composed of various compounds of chemicals such as cadmium, zinc, tellurium, selenium and sulfur. Quantum dots are routinely less than 500 nanometers in size. These nanoparticles react to electricity or light by emitting their own light across the visible range of wavelengths, e.g., from 470 to 730 nm. The applications for quantum dots include certain biomedical applications, e.g., medical sensors. By exploiting the unique optical properties of quantum dots, the conjugation of quantum dots with, for example, photosensitizers, targeting agents, and the like, also provides versatile multifunctional nanoparticles for both diagnostic imaging and therapeutic applications. In proof-of-concept experimentation, glucan particles were loaded with quantum dots composed of CDSe/ZnS. The particular quantum dots had a CDSe/ZnS core/shell structure, a size of approximately 3.5 nm (with an approximately 10 nm hydrodynamic size, $\lambda_{exc}=580$ nm, $\lambda_{em}=605$ nm. The quantum dots were loaded into the glucan particles by physical trapping techniques that include Qdot aggregation and entrapment within ovalbumin-RNA, dextran sulfate-chitosan and/or calcium alginate core matrices inside glucan particles. GP quantum dot formulations provide proof of concept loading and receptor-targeted cellular delivery of quantum dots for imaging and drug delivery applications. GP-QD (with or without alginate trapping) loading and uptake into cells (3T3-D1 cells) was visualized using standard fluorescent microscopy.

In further proof-of-concept experimentation, quantum dots with a surface charge were loaded into the glucan particles by electrostatic trapping techniques that included trapping the loaded quantum dots with PEI. The particular quantum dots had a CDSe/ZnS core/shell structure, and were carboxylated (Ocean Nanotech, Springdale, Ark.) The carboxylated NPs allowed for electrostatic trapping (via PEI) of the NPs in GPs. Demonstration of GP quantum dot loading and uptake into cells was visualized using fluorescent microscopy. In further proof-of-concept experimentation, quantum dots were surface loaded onto the glucan particles by affinity trapping techniques that include trapping the loaded biotinylated quantum dots with streptavidin and biotin (or PEI-biotin). The ability of biotinylated quantum dots to bind to biotinylated GP surfaces (and/or to GP encapsulated biotinylated nanocores) can be observed microscopically. The GP shells can be mixed with payloads such as tRNA followed by incubation with PEI-biotin to form biotinylated nanocores. Alternatively, the glucan shell matrix can be derivatized with biotin to form GP-biotin shells. GP-biotin shells can be synthesized by treating GPs with oxidizing agents such as periodate followed by Schiff base formation with amines such as biotin-$NH_2$, and reducing the Schiff base using reducing agents such as sodium borohydride. GP-biotin shells and GP biotinylated nanocores can be incubated with streptavidin, washed and then incubated with biotinylated quantum dots. Following washing the affinity loading of biotinylated quantum dots can be visualized by fluorescence microscopy. GP biotinylated nanocore-biotinylated quantum dot formulations provide proof of concept encapsulation by affinity trapping and receptor-targeted cellular delivery of quantum dots for imaging and drug delivery applications. GP-biotin quantum dot formulations provide proof of concept external shell loading and receptor-targeted cellular delivery of quantum dots for imaging and drug delivery applications. Proof-of-concept experimentation featured CdSe/ZnS core/shell structure quantum dots of approximately 20 nm hydrodynamic size, biotin derivatized (Invitrogen). In surface loading embodiments, streptavidin was used to allow for further attachment of biotinylated Qdots to GP surfaces. Visualization of GP quantum dot loading (GP surface loaded Qdots and GP encapsulated Qdots) and uptake into cells (RAW264 cells) was made via fluorescent microscopy.

I. Magnetic Nanoparticles

In some embodiments, the YCWPs (e.g., YCPs or GPs) can be loaded with magnetic nanoparticles. The magnetic particles can have paramagnetic or ferromagnetic properties.

To prepare YCWP (e.g., GP) magnetic nanoparticle formulations, empty GPs can be taken in tubes followed by loading with cationic magnetic nanoparticles or anionic magnetic nanoparticles (Ferrotec, Bedford, N.H.). The tubes can be frozen and dried, for example, by lyophilization, followed by pushing the nanoparticles into the hollow GP cavity with a solvent such as water. These steps can be repeated multiple times if necessary to push the magnetic particles all the way inside the GP shells. Resuspension in a solvent such as ethanol, followed by centrifugation can be employed to remove unbound or unencapsulated nanoparticles. The steps of lyophilization, pushing with solvent, incubation, resuspension and centrifugation can be repeated as necessary.

In certain embodiments, glucan particles can be loaded with magnetic nanoparticles such as for example, iron oxides. PEI can be used for trapping anionic magnetic nanoparticles. The magnetic nanoparticles can be compatible with living tissues and can be utilized in diagnostic and monitoring techniques such as radiology and imaging. In certain embodiments, the iron oxides can be mixtures of $Fe_3O_4$ and gamma-$Fe_2O_3$. In exemplary experimentation, magnetic nanoparticles were loaded into GPs. Ferrofluids (Ferrotec) of 10 nm diameter were purchased as stable colloidal suspensions in water. The cores of these particles are made of iron oxides which are known to be compatible with living tissues. From the X-ray measurements, the iron oxides are identified to be a mixture of $Fe_3O_4$ and gamma-$Fe_2O_3$. Particles can further comprise a surfactant polymer coat (either cationic or anionic) to prevent aggregation. Visualization of YCWPs (e.g., GPs) loaded with magnetic nanoparticles, their magnetic properties, and their uptake into cells can be made via phase contrast microscopy. GP-anionic magnetic nanoparticles trapped with fluorescent rhodamine PEI were visualized as was their uptake into cells (3T3-D1 cells) via fluorescent microscopy, and magnetic attraction (visible in microtubes containing the GP-NPs when placed adjacent to an appropriate magnet.) GP magnetic nanoparticle formulations provide proof of concept loading and receptor-targeted cellular delivery of magnetic nanoparticles for imaging, cell purification and drug delivery applications.

Figure 2B:
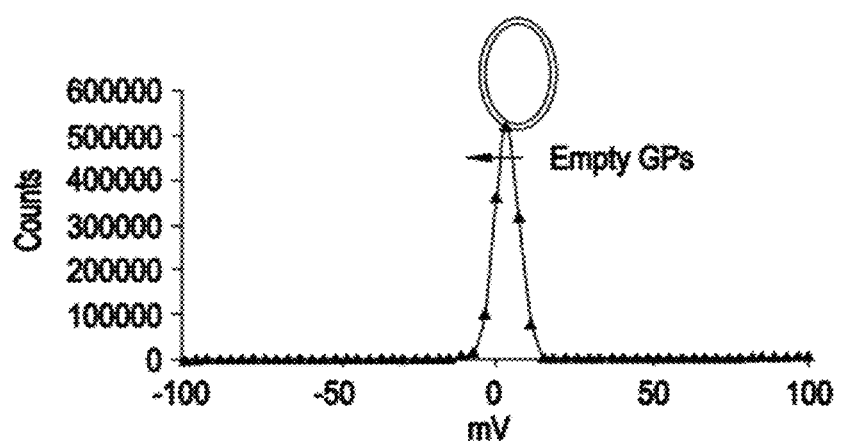
FIG. 2B shows characterization by Zeta potential of empty GP formulations.
Figure 3A:
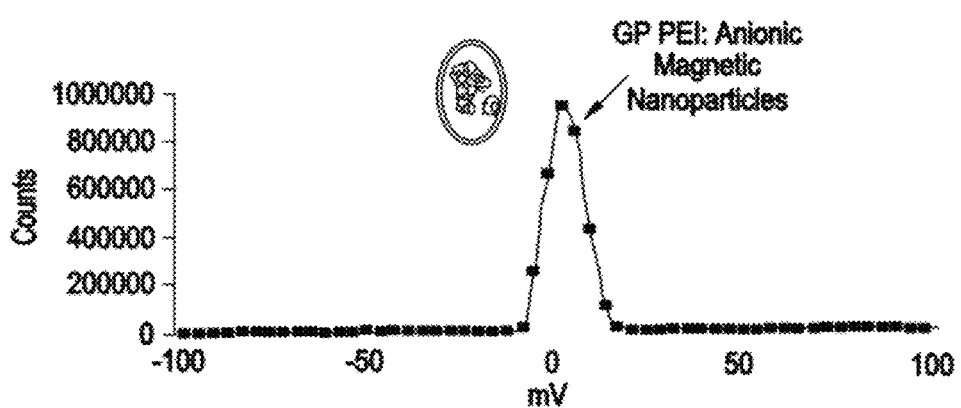
FIG. 3A depicts characterization by Zeta potential of anionic magnetic nanoparticles+GP formulations with PEI (clean magnetic GP sample.) FIG. 3B graphically depicts characterization by Zeta potential of anionic magnetic nanoparticles+GP formulations with PEI contaminated with free nanoparticles (magnetic GP sample with free nanoparticles).
Figure 3B:
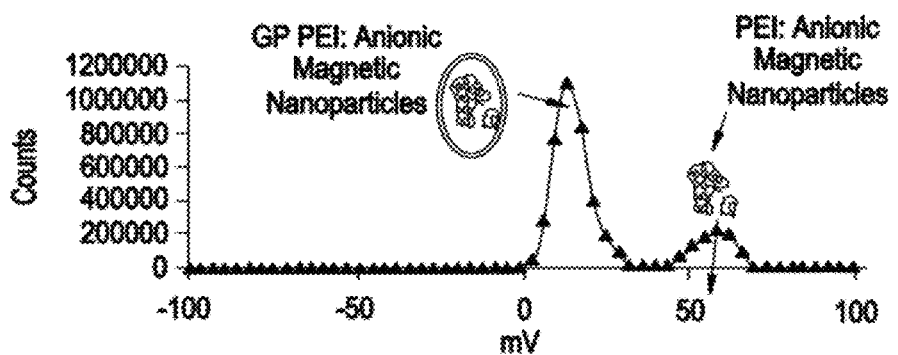
FIG. 3 graphically the characterization of magnetic GP formulations by Zeta Potential.
Figure 4:
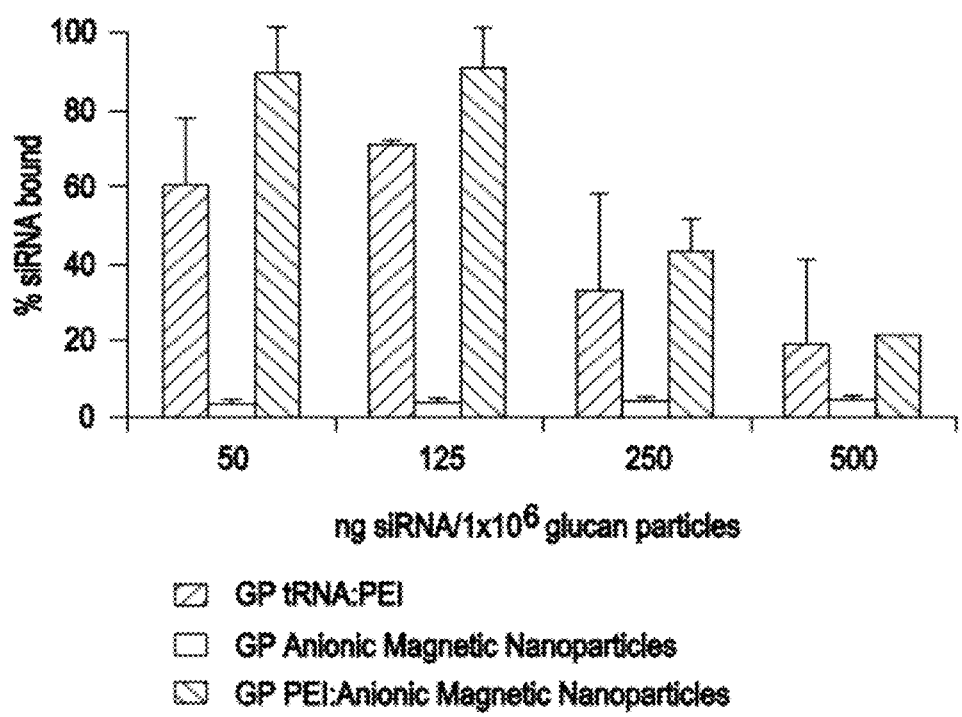
FIG. 4 graphically depicts the % of siRNA bound to GPs loaded with different magnetic nanoparticles (GP-magnetic nanoparticle/PEI siRNA binding.)

In some embodiments, the GP magnetic nanoparticle formulations can be characterized by measurement of their zeta potential. FIGS. 2A, 2B, 3A, and 3B show the characterization of magnetic nanoparticles GP formulations by zeta potential. FIG. 4 shows the % of GP-magnetic nanoparticle/PEI bound to siRNA. These results show that GP magnetic nanoparticle formulations can be synthesized to co-load a payload such as siRNA, DNA and proteins.

In some embodiments, commercially available ferrofluids from Ferrotec Corporation (Bedford, N.H.) can be used. A "ferrofluid" is a stable suspension of submicron size magnetic particles in various carrier liquids. These particles can be coated with stabilizers to prevent agglomeration. The physical properties of ferrofluids, such as volatility, environmental capability and viscosity, etc., are mostly determined by the choice of the carrier. When a magnetic field is applied, a ferrofluid acquires a net magnetic moment due to the orientation of particles in the field direction. These fluids exhibit no remanence or hysteresis. The maximum obtainable moment per unit volume is proportional to the loading density of the magnetic material and is characterized in ferrofluid products as the saturation magnetization value. At saturation, all the particles have their magnetic moments aligned with the external field. Above saturation, the magnetization of fluid is independent of the applied field.

In certain embodiments, the magnetic nanoparticles, can be 10 nm in diameter. In various embodiments, stable colloidal suspensions in water can be used. In some embodiments, the cores of the particles can be made of iron oxides which are known to be compatible with living tissues. The iron oxides have been identified as a mixture of $Fe_3O_4$ and gamma-$Fe_2O_3$. In certain embodiments, a surfactant polymer coat (either cationic or anionic) can be used to prevent aggregation, facilitate payload loading or polymer trapping.

J. Gold Nanoparticles

In certain embodiments, the glucan particles can be loaded with gold nanoparticles. Commercially available NanoXact™ (San Diego, Calif.) gold particles can be used to prepare formulations containing high quality spherical gold nanoparticles that are about 10-100 nm in size. More preferably, the gold nanoparticles are about 10-50 nm in size, e.g., 10 nm, 20 nm, 30 nm or 40 nm). The gold particles can be suspended, for example, in water at a mass concentration of about 0.05 mg/mL gold. The gold nanoparticles can be treated with MUA (11-mercaptoundecanoic acid), for example, at 0.1 mg/mL MUA, to form Au-MUA nanoparticles. Exemplary experimentation featured trapping of the Au-MUA nanoparticles into the glucan particles using PEI for trapping. In some embodiments, non-fluorescent nanoparticles for example, gold nanoparticles can be reacted with reagents to form the corresponding fluorescent nanoparticles. In certain embodiments, non-fluorescent Au-MUA nanoparticles can be reacted with cationic fluorescent PEI to provide the corresponding fluorescent nanoparticles. In exemplary experimentation, Au-MUA NPs (10 nm), trapped with rhodamine-PEI, were made. Visualization of GPs loaded with gold nanoparticles and their uptake into cells was via fluorescent microscopy. In certain embodiments GP-gold nanoparticle-MUA coated with PEI can be used to bind nucleic acids, such as siRNA. Au/MUA NPs (10 nm) were made using tRNA:PEI or PEI (alone) trapping. FIG. 4 shows the % of input fluorescent siRNA bound to GP-gold nanoparticle/PEI with or without the various trapping methodologies.

The trapping of Au/MUA nanoparticles within GPs can be evaluated using rhodamine-labeled PEI (rPEI) at different concentrations. An assay can be optimized to measure and quantify the amount of bound r-PEI. 10, 30, 40, 50, and 100 nm of NanoXact™ gold nanoparticles can be used for the evaluation. The gold nanoparticles can be taken in several tubes. Diluted alkaline solution and MUA solution can be added to the tubes followed by incubation to coat the gold particles with MUA. Centrifugation followed by washing with saline solution can remove the unbound material. The gold nanoparticles can then be carefully recovered by resuspension in saline and water followed by centrifugation. The absorption of the recovered gold nanoparticles can be measured to calculate the % recovery.

Empty GPs can be taken in tubes and suspensions of gold-MUA nanoparticles can be added. Incubation followed by freezing, drying, for example, by lyophilization, and pushing with water can result in GPs loaded with the gold-MUA nanoparticles. The steps can be repeated if necessary. An appropriate amount of payload trapping molecule such as rPEI can be added. Incubation, centrifugation and washing can remove the unbound material. The samples can be resuspended in saline solution and the number of GP Au-MUA nanoparticles-rPEI can be counted using a hematocytometer. The uptake of the GP Au-MUA-r-PEI into cells such as 3T3-DI cells can be measured and intracellular trafficking studied. GP gold nanoparticle formulations provide proof of concept loading and receptor-targeted cellular delivery of gold nanoparticles for imaging, cell ablation and drug delivery applications.

K. Virus-Associated Nanoparticles

In some embodiments, the glucan particles can be loaded with viruses such as for example, adeno-associated virus (AAV), or virus-like particles (VLPs), or any other small virus or virus particle. Sub-hydrodynamic volume loading can be employed to load the virus into the GP. Once inside the GP, the virus can be sequestered using heparin trapping by which heparin-virus complexes are formed inside the GP shell. According to an exemplary embodiment, a yeast cell wall particle-virus nanoparticle (YCWP-virus NP) delivery system can be produced, comprising yeast cell wall particles (YCWPs) comprising viral nanoparticles, wherein the YCWP delivery system is prepared by a process comprising the steps of incubating YCWPs with virus nanoparticles (e.g., adeno-associated virus (AAV), or virus-like particles (VLPs), or any other small virus or virus particle) together in solution for a time sufficient for the NPs to enter the YCWPs (e.g., YGPs), for example, for about 1-2 hours, optionally trapping the virus nanoparticles in the YCWPs using an appropriate trapping means, and washing and/or dispersing the resulting material such that the YCWP delivery system is prepared. In exemplary embodiments, the trapping means is heparin.

In some embodiments, virions of about 20-30 nm (e.g., 26 nm AAV virions encoding green fluorescent protein (GFP)) can be loaded into YCWPs (e.g., YGP). In certain embodiments, heparin can be used for trapping (e.g., 1-100 mg/ml heparin). Dilutions of the virus can be prepared using buffers such as PBS. The diluted virus solutions can be added to an appropriate amount of GPs in tubes. The tubes can be incubated during which time the GPs can swell and absorb the virus solution. Heparin in buffered solution can be added to trap the encapsulated virus. Incubation, sonication, centrifugation, and resuspension steps can be performed. Different amounts of the solution can be taken in for example, 96 well places to assess GFP transduction. Fluorescent microscopy can be used to detect the GFP fluorescence at different time intervals to monitor and assess the transduction efficiency.

Exemplary experimentation demonstrated loading of AAV2 into glucan particles. GPs were loaded with $10^{14}$ AAV2-GFP virions/mL (hydronamic volume loading) to allow particles to load into GPs, followed by heparin trapping (heparin-AAV2 complexes are trapped inside GPs. The presence of heparin-AAV2 aggregates inside the GPs was confirmed by microscopic visualization. GPs made according to this methodology were capable of delivering AAV to cells (3T3-D1 cells.) Moreover, the GP-AAV was as effective as free virus at transducing 3T3-D1 cells to express GFP. In the presence of free heparin, free virus transduction was >90% inhibited. AAV2-GFP (56% transfection), AAV2-GFP+heparin (4% transfection), GP AAV-GFP/heparin (54% transfection). GP AAV can also be resistant to neutralizing AAV antibodies potentially overcoming a major limitation of AAV gene therapy.

V. Methods of Use

The nanoparticles of the invention can be used in a variety of pharmaceutical applications for example treatment of diseases, as diagnostic agents for imaging, detecting and/or monitoring conditions such as plaque formation, tumor growth and tissue damage. The GPs of the invention can be used to deliver the encapsulated nanoparticles to the appropriate target when the nanoparticles can be released to carry out their intended drug delivery function.

A skilled artisan appreciates the applications of nanoparticles in biomedical imaging. For example, nanoparticles of compounds containing iodine or barium have been extensively used as contrast agents in diagnostic imaging using techniques such as X-ray, magnetic resonance imaging (MRI), ultrasound imaging and nuclear medicine. See U.S. Pat. No. 6,540,981.

Systems are methods are available to a skilled artisan to effectively use nanoparticles as imaging agents. See e.g., U.S. Pat. No. 7,110,585. Fluorescent nanoparticles have been employed in thermal imaging to measure "Stokes radiation" or "Stokes emission" characterized by optical absorption bands of the nanoparticles. See U.S. Pat. No. 7,413,341.

The present invention provides a method for the determination of temperature at one or more locations in a sample. The method comprises the use of a sample having a fluorophore, such as, for example, a fluorescent dye, fluorescent nanoparticle, or fluorescent protein, present at a location to be thermally measured. The fluorophore is characterized by having an optical absorption band which, when stimulated, results in the emission of a spectrum of fluorescence radiation, i.e., "Stokes radiation" or "Stokes emission."

The nanoparticles of the invention such as fluorescent polystyrene nanoparticles, magnetic nanoparticles and gold nanoparticles can be used for detecting and imaging tumors. A variety of techniques such as fluorescence spectroscopy, magnetic resonance imaging, surface enhanced raman spectroscopy, ultrasound, positron emission tomography, photoacoustic imaging and X-ray imaging can be used to detect the presence of the nanoparticles and monitor the extent to which they spread within the target tissue or organ.

In certain biomedical applications, magnetic nanoparticles, e.g., those found in ferrofluids, can be used either directly or as a component of one or more systems of the invention, in conjunction with a desired biologically active species, e.g., payload. The magnetic properties of these particles allow them to be rapidly separated from complex liquid mixtures even by relatively weak magnetic fields. Depending on the nature of the system, viruses, proteins, and or cells may be selectively separated. Therapeutic agents can be incorporated into or onto the magnetically active particles. The particles can concentrated by magnetic fields at specific body sites, for example, where they deliver high local concentration of drug.

A. Methods of Treatment

Routes of administration include but are not limited to oral; buccal, sublingual, pulmonary, transdermal, transmucosal, as well as subcutaneous, intraperitoneal, intravenous, and intramuscular injection. Preferred routes of administration are oral, pulmonary, intravenous and transdermal.

The particulate delivery system of the present invention is administered to a patient in a therapeutically effective amount. The particulate delivery system can be administered alone or as part of a pharmaceutically acceptable composition. In addition, a compound or composition can be administered all at once, as for example, by a bolus injection, multiple times, such as by a series of tablets, or delivered substantially uniformly over a period of time, as for example, using a controlled release formulation. It is also noted that the dose of the compound can be varied over time. The particulate delivery system can be administered using an immediate release formulation, a controlled release formulation, or combinations thereof. The term "controlled release" includes sustained release, delayed release, and combinations thereof.

A pharmaceutical composition of the invention can be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient that would be administered to a patient or a convenient fraction of such a dosage such as, for example, one-half or one-third of such a dosage.

In addition, a particulate delivery system of the present invention can be administered alone, in combination with a particulate delivery system with a different payload, or with other pharmaceutically active compounds. The other pharmaceutically active compounds can be selected to treat the same condition as the particulate delivery system or a different condition.

Another aspect of the invention relates to a kit comprising a pharmaceutical composition of the invention and instructional material. Instructional material includes a publication, a recording, a diagram, or any other medium of expression which is used to communicate the usefulness of the pharmaceutical composition of the invention for one of the purposes set forth herein in a human. The instructional material can also, for example, describe an appropriate dose of the pharmaceutical composition of the invention. The instructional material of the kit of the invention can, for example, be affixed to a container which contains a pharmaceutical composition of the invention or be shipped together with a container which contains the pharmaceutical composition. Alternatively, the instructional material can be shipped separately from the container with the intention that the instructional material and the pharmaceutical composition be used cooperatively by the recipient.

For example, a kit may comprise two separate pharmaceutical compositions comprising respectively a first composition comprising a particulate delivery system and a pharmaceutically acceptable carrier; and composition comprising second pharmaceutically active compound and a pharmaceutically acceptable carrier. The kit also comprises a container for the separate compositions, such as a divided bottle or a divided foil packet. Additional examples of containers include syringes, boxes, bags, and the like. Typically, a kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

A particulate delivery system composition, optionally comprising other pharmaceutically active compounds, can be administered to a patient either orally, rectally, parenterally, (for example, intravenously, intramuscularly, or subcutaneously) intracisternally, intravaginally, intraperitoneally, intravesically, locally (for example, powders, ointments or drops), or as a buccal or nasal spray.

Parenteral administration of a pharmaceutical composition includes any route of administration characterized by physical breaching of a tissue of a human and administration of the pharmaceutical composition through the breach in the tissue. Parenteral administration thus includes administration of a pharmaceutical composition by injection of the composition, by application of the composition through a surgical incision, by application of the composition through a tissue-penetrating non-surgical wound, and the like. In particular, parenteral administration includes subcutaneous, intraperitoneal, intravenous, intraarterial, intramuscular, or intrasternal injection and intravenous, intraarterial, or kidney dialytic infusion techniques.

Formulations for parenteral administration include suspensions, solutions, emulsions in oily or aqueous vehicles, pastes, and implantable sustained-release or biodegradable formulations. Such formulations can further comprise one or more additional ingredients including suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition. The pharmaceutical compositions can be prepared, packaged, or sold in the form of a sterile injectable aqueous or oily suspension or solution. This suspension or solution can be formulated according to the known art, and can comprise, in addition to the active ingredient, additional ingredients such as the dispersing agents, wetting agents, or suspending agents described herein. Such sterile injectable formulations can be prepared using a non-toxic parenterally-acceptable diluent or solvent, such as water or 1,3-butanediol, for example. Other acceptable diluents and solvents include Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer system. Compositions for sustained release or implantation can comprise pharmaceutically acceptable polymeric or hydrophobic materials such as an emulsion, an ion exchange resin, a sparingly soluble polymer, or a sparingly soluble salt.

Solid dosage forms for oral administration include capsules, tablets, powders, and granules. In such solid dosage forms, the particulate delivery system is optionally admixed with at least one inert customary excipient (or carrier) such as sodium citrate or dicalcium phosphate or (a) fillers or extenders, as for example, starches, lactose, sucrose, mannitol, or silicic acid; (b) binders, as for example, carboxymethylcellulose, alginates, gelatin, polyvinylpyrrolidone, sucrose, or acacia; (c) humectants, as for example, glycerol; (d) disintegrating agents, as for example, agar-agar, calcium carbonate, potato or tapioca starch, alginic acid, certain complex silicates, or sodium carbonate; (e) solution retarders, as for example, paraffin; (f) absorption accelerators, as for example, quaternary ammonium compounds; (g) wetting agents, as for example, cetyl alcohol or glycerol monostearate; (h) adsorbents, as for example, kaolin or bentonite; and/or (i) lubricants, as for example, talc, calcium stearate, magnesium stearate, solid polyethylene glycols, sodium lauryl sulfate, or mixtures thereof. In the case of capsules and tablets, the dosage forms may also comprise buffering agents.

Oral compositions can be made, using known technology, which specifically release orally-administered agents in the small or large intestines of a human patient. For example, formulations for delivery to the gastrointestinal system, including the colon, include enteric coated systems, based, e.g., on methacrylate copolymers such as poly(methacrylic acid, methyl methacrylate), which are only soluble at pH 6 and above, so that the polymer only begins to dissolve on entry into the small intestine. The site where such polymer formulations disintegrate is dependent on the rate of intestinal transit and the amount of polymer present. For example, a relatively thick polymer coating is used for delivery to the proximal colon (Hardy et al., 1987 Aliment. Pharmacol. Therap. 1:273-280). Polymers capable of providing site-specific colonic delivery can also be used, wherein the polymer relies on the bacterial flora of the large bowel to provide enzymatic degradation of the polymer coat and hence release of the drug. For example, azopolymers (U.S. Pat. No. 4,663,308), glycosides (Friend et al., 1984, J. Med. Chem. 27:261-268) and a variety of naturally available and modified polysaccharides (see PCT application PCT/GB89/00581) can be used in such formulations.

Pulsed release technology such as that described in U.S. Pat. No. 4,777,049 can also be used to administer the particulate delivery system to a specific location within the gastrointestinal tract. Such systems permit delivery at a predetermined time and can be used to deliver the particulate delivery system, optionally together with other additives that my alter the local microenvironment to promote stability and uptake, directly without relying on external conditions other than the presence of water to provide in vivo release.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, isotonic saline, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, almond oil, arachis oil, coconut oil, cottonseed oil, groundnut oil, corn germ oil, olive oil, castor oil, sesame seed oil, MIGLYOL™, glycerol, fractionated vegetable oils, mineral oils such as liquid paraffin, tetrahydrofurfuryl alcohol, polyethylene glycols, fatty acid esters of sorbitan, or mixtures of these substances, and the like. Besides such inert diluents, the composition can also include adjuvants, such as wetting agents, emulsifying and suspending agents, demulcents, preservatives, buffers, salts, sweetening, flavoring, coloring and perfuming agents. Suspensions, in addition to the active compound, may contain suspending agents, as for example, ethoxylated isostearyl alcohols, polyoxyethylene sorbitol or sorbitan esters, microcrystalline cellulose, hydrogenated edible fats, sodium alginate, polyvinylpyrrolidone, gum tragacanth, gum acacia, agar-agar, and cellulose derivatives such as sodium carboxymethylcellulose, methylcellulose, hydroxypropylmethylcellulose, aluminum metahydroxide, bentonite, or mixtures of these substances, and the like. Liquid formulations of a pharmaceutical composition of the invention that are suitable for oral administration can be prepared, packaged, and sold either in liquid form or in the form of a dry product intended for reconstitution with water or another suitable vehicle prior to use.

A pharmaceutical composition of the invention can be prepared, packaged, or sold in a formulation suitable for pulmonary administration via the buccal cavity. Such compositions are conveniently in the form of dry powders for administration using a device comprising a dry powder reservoir to which a stream of propellant can be directed to disperse the powder or using a self-propelling solvent/powder-dispensing container such as a device comprising the particulate delivery system suspended in a low-boiling propellant in a sealed container. Dry powder compositions may include a solid fine powder diluent such as sugar and are conveniently provided in a unit dose form. Low boiling propellants generally include liquid propellants having a boiling point below 65 degrees F. at atmospheric pressure. Generally the propellant can constitute 50 to 99.9% (w/w) of the composition, and the active ingredient can constitute 0.1 to 20% (w/w) of the composition. The propellant can further comprise additional ingredients such as a liquid non-ionic or solid anionic surfactant or a solid diluent (preferably having a particle size of the same order as particles comprising the particulate delivery system).

Pharmaceutical compositions of the invention formulated for pulmonary delivery can also provide the active ingredient in the form of droplets of a suspension. Such formulations can be prepared, packaged, or sold as aqueous or dilute alcoholic suspensions, optionally sterile, comprising the particulate delivery system, and can conveniently be administered using any nebulization or atomization device. Such formulations can further comprise one or more additional ingredients including a flavoring agent such as saccharin sodium, a volatile oil, a buffering agent, a surface active agent, or a preservative such as methylhydroxybenzoate.

The formulations described herein as being useful for pulmonary delivery are also useful for intranasal delivery of a pharmaceutical composition of the invention. Another formulation suitable for intranasal administration is a coarse powder comprising the particulate delivery system. Such a formulation is administered in the manner in which snuff is taken i.e. by rapid inhalation through the nasal passage from a container of the powder held close to the nares.

A pharmaceutical composition of the invention can be prepared, packaged, or sold in a formulation suitable for buccal administration. Such formulations can, for example, be in the form of tablets or lozenges made using conventional methods, and can, for example, comprise 0.1 to 20% (w/w) of a particulate delivery system, the balance comprising an orally dissolvable or degradable composition and, optionally, one or more of the additional ingredients described herein. Alternately, formulations suitable for buccal administration can comprise a powder or an aerosolized or atomized solution or suspension comprising the particulate delivery system.

The following examples illustrate the preparation of certain specific compounds according to the present technology. A skilled artisan appreciates that the invention is not limited to the exemplary work described or to the specific details set forth in the examples.

A skilled artisan further appreciates that the experimental conditions depicted in the following examples can be varied by as much as 2%, 5%, 10% or 20% above or below the listed amount, temperature, concentration, pH, time and rpm in order to optimize the conditions to achieve the desired results from the experiments.

EXAMPLES

Glucan particles have been used for macrophage-targeted delivery of a wide range of payload macromolecules (H. Huang, et al., *Infection and Immunity*, vol. 77, pp. 1774-1781, 2009, E. Soto, et al., *Bioconjugate Chemistry*, vol. 19, no. 4, pp. 840-848, 2008, M. Aouadi, et al., Nature, vol. 458, pp. 1180-1184, 2009, G. Tesz, et al., Biochemical Journal, vol. 436, pp. 351-362, 2011, E. Soto, et al., *Polymers*, vol. 2, pp. 681-689, 2010]. Soluble payloads can be efficiently encapsulated inside GPs by both polyplex and Layer-by-Layer (LbL) synthetic approaches. There is a growing interest to extend the use of the GP delivery technology for small drug molecules (i.e. chemotherapeutics and antibiotics). However, GPs have limitations in the encapsulation of small molecules as most of these molecules are neutral in charge and cannot be trapped by the non-covalent techniques used to assemble macromolecule polyplexes inside GPs. Also, hydrophobic drugs present a challenge for loading inside GPs. The combination of nanoparticle encapsulation technologies and glucan particles offers an attractive opportunity to extend the use of GPs for macrophage-targeted delivery of small molecule drugs. The following examples present the results of several systems using model nanoparticles to demonstrate the GP mediated nanoparticle delivery systems of the present invention.

Example 1

Test Ability of Biotinylated Qdots to Bind to Biotinylated YGP Surface and to GP Encapsulated Biotinylated Nanocores Experiments were conducted to test the ability of loading quantum dots (CDSe/ZnS quantum dots) into GP by affinity trapping or on the surface of the shell using biotin and streptavidin affinity interactions.

To prepare YGP tRNA/PEI-biotin cores, 1 mg of YGP was mixed with 6 µL 10 mg/mL yeast RNA (Sigma), and incubated 2 hours at room temperature. Then 250 µL of 0.1% PEI biotin was added and the particles allowed to swell for 30 min, then sonicated and incubated 1 hour at room temperature. The particles were collected by centrifugation, washed three times with 500 µL 0.9% saline and resuspended in 500 µL PBS. The particles were sonicated, particle number counted using a hemacytometer, a 1×10+8/mL suspension prepared in PBS and stored frozen at −20 C.

To bind streptavidin Q-Dots to YGP-biotin shells and YGP tRNA/PEI-biotin cores PBS, particles and Qdots were added as indicated in Table 1.

To assess Qdot loading, particles were imaged using a fluorescent microscope with rhodamine filters at 1000× magnification.

TABLE 1

| Tube | 1 × 10 + 8 YGP | uL | Formulation | μL 1/100 Qdots | μL PBS |
|---|---|---|---|---|---|
| 1 | YGP | 100 | GP tR/P-B | 0 | 150 |
| 2 | YGP | 100 | GP tR/P-B-Qdot | 10 | 140 |
| 3 | YGP-biotin | 100 | GP-biotin | 0 | 150 |
| 4 | YGP-biotin | 100 | GP-biotin-Qdot | 10 | 140 |
| 5 | Rhodamine-YGP | 100 | GP-TR | 0 | 150 |
| 6 | | 0 | Qdot | 10 | 240 |

To demonstrate intracellular delivery of YGP-biotin-streptavidin-biotinylated Qdot formulations particles were incubated with RAW264 cells at a 10 particle:cell ratio for 2 hrs., the cells were then washed with PBS and fixed in 0.1% formalin in PBS. Fluorescence microscopic images showed GP-biotin surface affinity loaded with quantum dots and their uptake by RAW264 cells. Fluorescence microscopic images showed GP biotinylated nanocores affinity loaded via streptavidin with encapsulated biotinylated Qdots and their uptake by RAW264 cells. The quantum dots were effectively affinity loaded both, on the surface, as well as inside the GP, and delivered into phagocytic RAW264 macrophage cells.

Example 2

Loading of GP with Magnetic Nanoparticles

Experiments were conducted to show that magnetic NPs could be loaded into or onto GPs. To make GP formulations loaded with magnetic nanoparticles tubes containing 1 mg or 100 mg of empty GPs were loaded with 5 μL of magnetic Nanoparticles/mg GP. Cationic 10 nm magnetic nanoparticles (EMG 607) or anionic 10 nm magnetic nanoparticles (EMG 707) were loaded (Ferrotec, Bedford, N.H.). Following incubation for 2 hr at room temperature tubes were frozen and lyophilized. A water push reaction was carried out with 5 μl water/mg GPs at room temperature for >1 hours. The tubes were then frozen and lyophilized, and contents resuspended in 70% ethanol for 15 minutes. Free nanoparticles were separated from GP magnetic nanoparticles by centrifugation and supernatants were collected and optical density measured to determine unencapsulated magnetic nanoparticles. The 70% ethanol washing steps were repeated twice and the pellets lyophilized. The pellets were then resuspended in the indicated amounts of primary trapping polymer (Table 2) and incubated for 1 h at room temperature. The second trapping polymer layer was added as indicated in Table 2 and incubated for 20 minutes at room temperature. The particles were collected by centrifugation and washed twice with 500 ul 0.9% saline. Supernatants were collected and optical density measured to determine any lost magnetic nanoparticles. The pellet containing the loaded particles was then resuspended in 0.9% saline and functionally purified using a magnet. Microscopy images showed empty GPs vs. GPs loaded with magnetic nanoparticles and purification of magnetic GPs by a magnet. Non-magnetic GPs were carefully removed by aspiration. The particles were then resuspended in 70% ethanol to sterilize overnight at −20 C. Then the particles were aseptically washed three samples in sterile 0.9% saline, sonicated, and particle number counted using a hemacytometer, Particles were diluted to prepare a 1×10+8/mL suspension in PBS and stored frozen at −20 C.

TABLE 2

| Tube | GP mg particles | Ferrotec NP | ul NP | Core polymer | uL | Trapping Polymer | mL |
|---|---|---|---|---|---|---|---|
| 1 | 100 | EMG 607 | 500 | 10 mg/mL tRNA | 500 | 1% 25 k rPEI | 2 |
| 2 | 100 | EMG 607 | 500 | 1 mg/mL Alginate | 500 | 1% 25 k rPEI | 2 |
| 3 | 100 | EMG 707 | 500 | 0.1% 25 k rPEI | 500 | 0.9% saline | 2 |
| 4 | 100 | EMG 707 | 500 | 0.1% 25 k rPEI | 500 | 0.1% 25 k rPEI | 2 |

To assess magnetic nanoparticle loading particles were imaged microscopically at 1000× magnification. Fluorescence microscopic visualization images showed GP loaded with anionic magnetic nanoparticles trapped with rhodamine PEI (rPEI). To demonstrate intracellular delivery of YGP-magnetic nanoparticles they were incubated with 3T3-D1 cells at a 10 particle:cell ratio for 1-24 hrs. Cells were then washed with PBS and fixed in 0.1% formalin in PBS. Fluorescence microscopic visualization images showed GP loaded with anionic magnetic nanoparticles and their uptake by 3T3-D1 cells.

To characterize the zeta potential of GP-Mag NPs suspensions were assayed using a Malvern DLS (Malvern Instruments, Worcestershire, UK) using manufacturer recommended methods. FIG. 2A shows characterization of the zeta potential of anionic magnetic nanoparticles+GP formulations with or without PEI. FIG. 2B shows characterization by Zeta potential of empty GP formulations. FIG. 3A shows characterization by Zeta potential of anionic magnetic nanoparticles+GP formulations with PEI prepared using the optimized loading method. FIG. 3B shows characterization by Zeta potential of magnetic GP sample with free nanoparticles using a loading method without the water push step. To determine if GP-anionic Mag NP-PEI complexed formulations could bind fluorescent siRNA, control GP RNA-PEI, GP-anionic Mag NP and GP-anionic Mag NP-PEI particle formulations were incubated with Cy3-labeled fluorescent siRNA at increasing concentrations. Following a 2 hr incubation at room temperature the particles were centrifuged and the amount of bound siRNA determined by fluorescence spectroscopy. FIG. 4 shows the % of fluorescent siRNA bound to GPs loaded with magnetic nanoparticles with and without a cationic PEI coat. As demonstrated in the instant example, the various magnetic nanoparticles were effectively loaded inside the GP and delivered intracellularly into cells capable of phagocytosing glucan particles. Moreover, GP-anionic Mag NP-PEI particle formulations effectively bound siRNA.

Example 3

GP Trapping of Au/MUA Nanoparticles

Gold nanoparticles coated with NanoXact™ Gold nanoparticles from Nanocomposix (San Diego, Calif.) (Table 3; 250 uL, 0.02 mg Au/mL) were incubated with 11-mercaptoundecanoic acid (MUA, 110 uL of a 0.6 mg/mL solution). The final volume was adjusted to 500 uL with 0.01 M NaOH. The samples were then incubated overnight at room temperature. The MUA derivatized gold nanoparticles (Au/MUA) were centrifuged for 20 min at 10000 rpm. The supernatant was carefully removed and the pellets were washed twice with 1 mM NaCl. The washed pellets were resuspended in 250 uL of 1 mM NaCl and OD measurement at 525 nm was used to calculate % of nanoparticle recovery.

TABLE 3

| Tube | Au NP size |
|---|---|
| 1 | Au 10 nm |
| 2 | Au 30 nm |
| 3 | Au 40 nm |
| 4 | Au 50 nm |
| 5 | Au 100 nm |

GP Loading of Au/MUA Nanoparticles—

Empty glucan particles were mixed with Au/MUA nanoparticles (5 uL of nanoparticle suspension/mg GP) as indicated in Table 4. The pellet was mixed and incubated at room temperature for 1 hour. The samples were then frozen and lyophilized. The Au/MUA nanoparticle loading was repeated two more times. The samples were water pushed with 5 ul of water/mg GP at room temperature for 1 hour. The samples were then frozen and lyophilized. Ethanol (70% v/v) was added (100 uL of ethanol/mg GP) and the sample was collected by centrifugation to remove the unencapsulated Au MUA nanoparticles. The pelleted GP Au MUA nanoparticle samples were frozen and lyophilized. Rhodamine labeled PEI (rPEI) was then added (5 uL of 0.01% rPEI/mg GP) to coat the Au/MUA nanoparticles. The samples were incubated for 20 minutes followed by addition of 100 uL of 0.01% rPEI/mg GP. The samples were allowed to swell in the rPEI, particles were sonicated and incubated for additional 30 minutes. GP-Au/MUA/rPEI formulations were purified by centrifugation to remove unbound rPEI and free nanoparticles. The samples then washed three times with 0.9% saline and evaluated microscopically at 1000× magnification for evidence of fluorescent Au/MUA/rPEI core formation inside GPs. Samples that showed evidence of core formation were sterilized in 70% ethanol overnight at −20 C. Following sterilization the samples were aseptically washed three times in 0.9% saline, resuspended in 1 mL 0.9% saline, counted with a hematocytometer and the particle concentration diluted to 1×10+8 part/mL. The GP-Au/MUA/rPEI formulations were tested for uptake into 3T3-D1 cells and for siRNA binding.

TABLE 4

| Tube | Au NP | ul NP | PEI | uL PEI | uL PEI |
|---|---|---|---|---|---|
| 1 | Au10/MUA | 5 | 0.01% | 5 | 100 |
| 2 | Au30/MUA | 5 | 0.01% | 5 | 100 |
| 3 | Au40/MUA | 5 | 0.01% | 5 | 100 |
| 4 | Au50/MUA | 5 | 0.01% | 5 | 100 |
| 5 | Au100/MUA | 5 | 0.01% | 5 | 100 |
| 6 | 0.9% saline | 5 | 0.01% | 5 | 100 |
| 7 | Au10/MUA | 5 | 0.10% | 5 | 100 |
| 8 | Au30/MUA | 5 | 0.10% | 5 | 100 |
| 9 | Au40/MUA | 5 | 0.10% | 5 | 100 |
| 10 | Au50/MUA | 5 | 0.10% | 5 | 100 |
| 11 | Au100/MUA | 5 | 0.10% | 5 | 100 |
| 12 | 0.9% saline | 5 | 0.10% | 5 | 100 |
| 13 | Au10/MUA | 5 | 1% | 5 | 100 |
| 14 | Au30/MUA | 5 | 1% | 5 | 100 |
| 15 | Au40/MUA | 5 | 1% | 5 | 100 |
| 16 | Au50/MUA | 5 | 1% | 5 | 100 |
| 17 | Au100/MUA | 5 | 1% | 5 | 100 |
| 18 | 0.9% saline | 5 | 1% | 5 | 100 |
| 19 | Au 10 nm | 5 | 0.01% | 5 | 100 |
| 20 | Au 10 nm | 5 | 0.10% | 5 | 100 |
| 21 | Au 10 nm | 5 | 1% | 5 | 100 |
| 22 | Au 50 nm | 5 | 0.01% | 5 | 100 |
| 23 | Au 50 nm | 5 | 0.10% | 5 | 100 |
| 24 | Au 50 nm | 5 | 1% | 5 | 100 |

Figure 5:
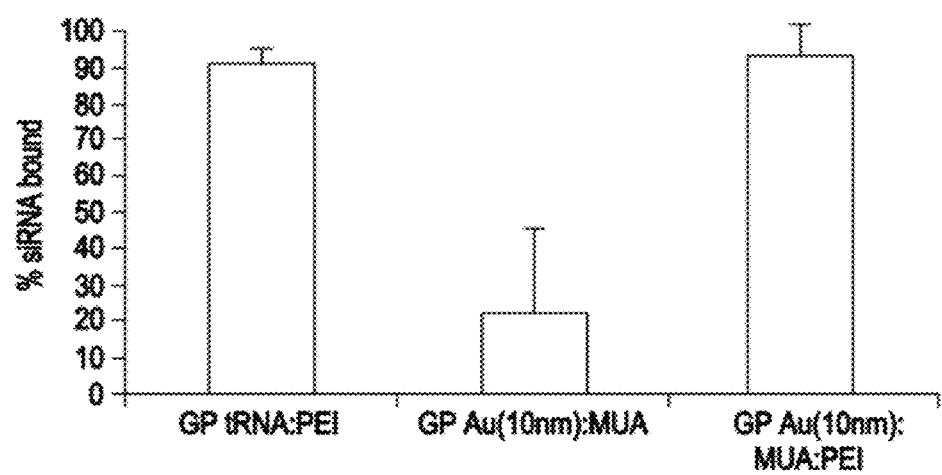
FIG. 5 is a graph depicting the % of siRNA bound to GPs loaded with tRNA-PEI vs. AU-MUA vs. Au-MUA-PEI (GP-Au/MUA/PEI siRNA binding.)

Fluorescence microscopic visualization images showed GP loaded with gold-MUA-rPEI nanoparticles and their uptake by 3T3-D1 cells. FIG. 5 shows the % of siRNA bound to GPs loaded with tRNA-PEI vs. AU-MUA vs. Au-MUA-PEI. The Au-MUA and Au-MUA-rPEI nanoparticles were effectively loaded inside the GP and delivered into the phagocytic cells. Moreover, the GP Au-MUA-rPEI nanoparticles effectively bound fluorescent siRNA.

Example 4

GP Loading of AAV2-GFP and GFP Transfection

Experiments were conducted to demonstrate loading adeno associated virus-2 (AAV2-GFP) into GP with heparin trapping to form Heparin-AAV2 complexes trapped inside GPs. AAV2-GFP virus dilutions containing 1×10+12, 1×10+11, 1×10+10 genome equivalents/mL were made in PBS. One uL of each AAV2-GFP dilution was added to 0.2 mg GP and allowed to swell and absorb the virus for 2 hrs at 4 C. As indicated in Table 5 100 uL of 10 mg/mL heparin in PBS was added to trap the virus. The tubes were incubated for 1 hr at 4 C. Samples for electron microscopy were collected by centrifugation and pellet frozen and supplied to the UMMS Imaging Core. The samples were embedded, fixed, sectioned and imaged by transmission electron microscopy. Samples for GFP transduction experiments were diluted in DMEM medium+10% fetal calf serum and 1% penicillin-streptomycin and 1% glutamine as indicated in Table 5. The particles were then lightly sonicated and 1, 3.3 or 10 uL of each formulation were added to a 96 well plate containing 1×10+4 3T3-D1 cells/well+/−100 ug/ml heparin to assess GFP transduction. Cells were imaged at 48 and 96 hrs by fluorescent microscopy to assess GFP transduction efficiency.

TABLE 5

| Tube | GP | 1 ul AAV2-GFP dilution | 10 mg/ml heparin | ul DMEM |
|---|---|---|---|---|
| 1 | | | | 1000 |
| 2 | | AAV 2 0.01X | | 1000 |
| 3 | | AAV 2 0.1X | | 1000 |
| 4 | | AAV 2 1X | | 1000 |
| 5 | | AAV 2 0.01X | 100 | 900 |
| 6 | | AAV 2 0.1X | 100 | 900 |
| 7 | | AAV 2 1X | 100 | 900 |
| 8 | 0.2 mg | | | 1000 |
| 9 | 0.2 mg | | 100 | 900 |
| 10 | 0.2 mg | AAV 2 0.01X | 100 | 900 |
| 11 | 0.2 mg | AAV 2 0.1X | 100 | 900 |
| 12 | 0.2 mg | AAV 2 1X | 100 | 900 |

Electron microscopic visualization images showed empty GPs compared to GPs loaded with AAV2-heparin. The presence of AAV2-heparin complexes inside the glucan shell cavity could clearly be seen via electron microscopic visualization. Fluorescence microscopic visualization images showed 3T3-D1 cells transduced with AAV2 GFP vs. AAV2-GFP+heparin vs. GP AAV2-GFP/heparin and the GFP transduction efficiency of these formulations. The heparin-AAV2 complexes were effectively loaded inside the GP and could efficiently transduce 3T3-D1 in the presence of viral uptake inhibitor, heparin.

Example 5

Covalently Linking Trapping Polymers to GP Surface

TP-GP

Figure 6A:
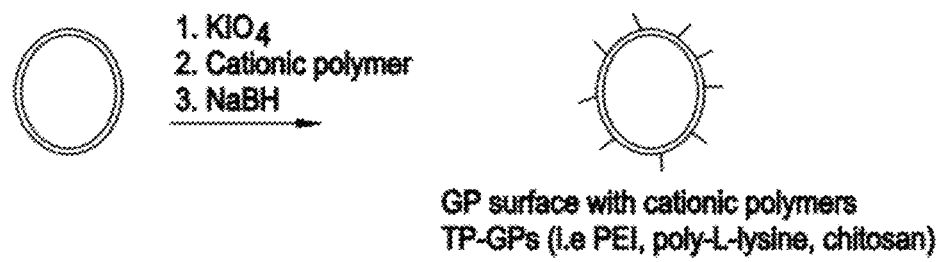
FIG. 6A depicts an exemplary scheme describing covalent coupling of cationic polymers to GP via reductive amination.
Figure 6B:
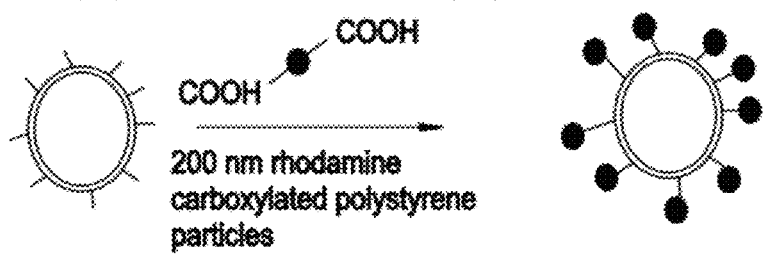
FIG. 6B depicts an exemplary scheme describing non-covalent binding of rhodamine carboxylated polystyrene nanoparticles to GPs.

FIG. 6A shows an exemplary scheme describing covalent coupling of cationic polymers to GP via reductive amination.

Dry GPs were resuspended in potassium periodate (1 mL of a 1 mg/mL solution/mg GP). The mixture was stirred in the dark at room temperature for at least 8 hours. The suspension was then centrifuged and the supernatant layer was removed. The pellet was washed three times with water to remove residual potassium periodate and the particles were resuspended in water at a concentration of 20 mg/mL. Aliquots of 250 uL (5 mg GPs) were prepared for labeling with different cationic polymers. The oxidized GP samples were treated with the amounts of polymer indicated in Table 6. The reaction mixtures were stirred at room temperature for 24 h. Sodium borohydride (30 mg $NaBH_4$/mg GP) was added to each tube and the suspension was stirred for 24 h. The sodium borohydride reduction step was repeated by adding a second addition of sodium borohydride (30 mg/mg GP) and stirring was continued for an additional 24 h. The mixture was centrifuged and the supernatant portion was discarded. The modified GPs were washed 3 times with water. Tris buffer (2.5 mL) was added and the samples stirred for 30 minutes. The samples were then washed 3 times with water, resuspended in 10 mL of 70% ethanol, and sterilized overnight at −20° C. The sterilized TP-GP samples were aseptically washed 3 times in 10 mL of 0.9% saline. The samples were finally resuspended in 10 mL of 0.9% saline, counted with a hematocytometer and the particle concentration diluted to 1×10+8 part/mL. Trapping polymer-derivatized GP samples were evaluated for binding of anionic fluorescent polystyrene (200 nm) nanoparticles (Invitrogen, Carlsbad, Calif.).

TABLE 6

| Tube | Polymer | Concentration TP (% w/v) | mL TP |
|---|---|---|---|
| 1 | 100k PEI | 10 | 5.27 |
| 2 | 25k PEI | 10 | 1.4 |
| 3 | 25k r-PEI | 10 | 1.4 |
| 4 | 25k f-PEI | 10 | 1.4 |
| 5 | 10k PEI | 1 | 5.3 |
| 6 | 10k r-PEI | 1 | 5.3 |
| 7 | 10k f-PEI | 1 | 5.3 |
| 8 | 2.5k PEI | 1 | 1.3 |
| 9 | 1.8k PEI | 1 | 0.95 |
| 10 | 1.2k PEI | 1 | 0.63 |
| 11 | 0.6k PEI | 1 | 0.32 |
| 15 | Chitosan | 1 | 5.27 |
| 16 | Polylysine (PLL) | 1 | 5.27 |

Example 6

Figure 7A:
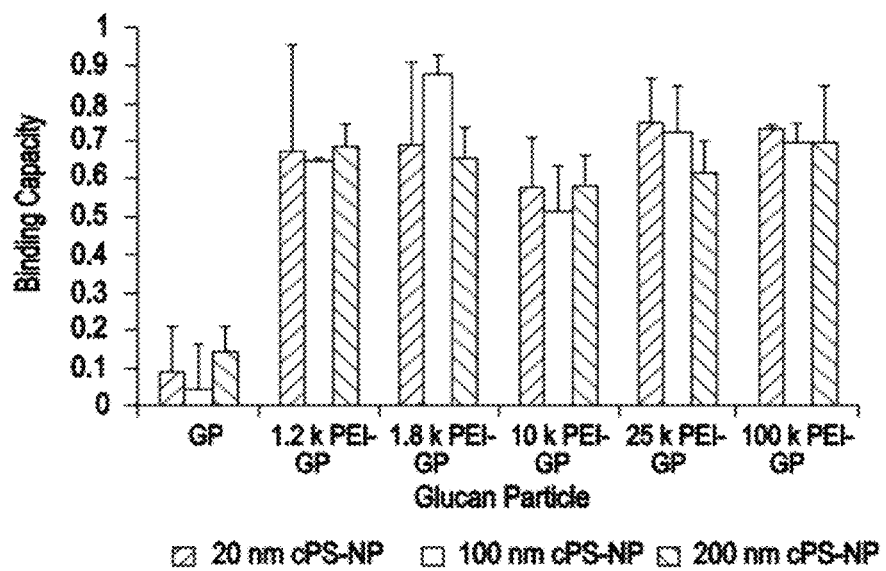
FIG. 7A graphically depicts the binding efficiency of GPs derivatized with different molecular weights of PEI for anionic fluorescent polystyrene nanoparticles of 20, 100, and 200 nm in diameter (experimental results were obtained at a cPS-NP/GP ratio of 100:1, the values correspond to average of at least five samples).

Electrostatic Binding of 200 nm Anionic Fluorescent Polystyrene Nanoparticles to Trapping Polymer-Derivatized GP FIG. 7 shows an exemplary scheme describing non-covalent binding of rhodamine carboxylated 200 nm polystyrene nanoparticles to GPs.

Trapping polymer-derivatized GPs (10 uL of 1×10+8 particles/mL) were mixed with 10 uL of 1×10+10 anionic fluorescent polystyrene nanoparticle and 80 uL 0.9% saline. The particles were incubated at room temperature for 2 hours and then centrifuged at 10,000 rpm for 3 min. The samples were washed once with 0.9% saline and the supernatants were collected to measure the fluorescence of unbound polystyrene nanoparticles. The pellets containing the polystyrene-cationic polymer-derivatized GPs were resuspended in 100 uL 0.9% saline and fluorescence measured to quantify the % of fluorescent polystyrene nanoparticles bound to the cationic polymer-derivatized GPs. The fluorescent 200 nm polystyrene-cationic polymer-derivatized GPs were imaged by fluorescent microscopy to demonstrate the binding of 200 nm anionic nanoparticles on the cationic GP surface. The fluorescent 200 nm polystyrene-cationic polymer-derivatized GPs were incubated with 3T3-D1 cells for 3 hrs, cells fixed in 0.1% formalin and imaged by fluorescent microscopy. Fluorescence microscopic visualization images illustrated the GP surface localization of cationic polymer surface-derivatized GPs incubated with fluorescent 200 nm polystyrene nanoparticles, and their uptake by 3T3-D1 cells. Fluorescence microscopic visualization images showed underivatized GPs with fluorescent 200 nm polystyrene nanoparticles illustrating the absence of binding of the polystyrene nanoparticles to the GP surface. FIG. 7 shows the % of rhodamine carboxylated polystyrene nanoparticles binding to cationic polymer surface-derivatized GPs. Binding of 200 nm polystyrene particles to TP-GP (y-axis represents % of different sized NPs in the pellet after sucrose cushion separation of pellet from supernatant. The instant experimentation demonstrated that fluorescent polystyrene nanoparticles of different sizes too large to enter into the hollow GP cavity were effectively loaded on the surface of the GP and delivered into cells.

Example 7

Glucan Particles Loaded with Derivitized Polymeric Nanoparticles

Figure 8A:
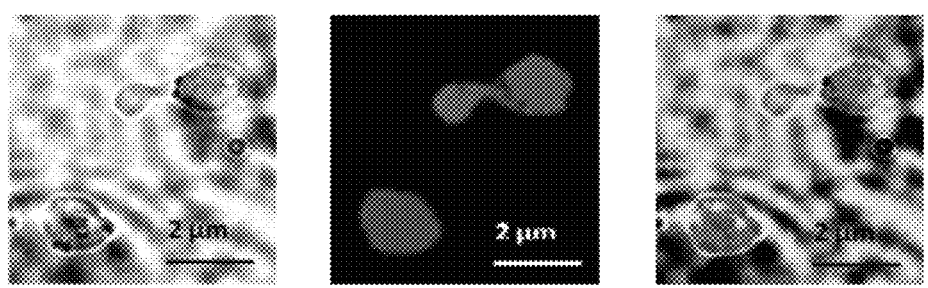
FIG. 8A depicts microscopic images of GPs containing 20 nm anionic fluorescent carboxylate polystyrene nanoparticles.
Figure 8B:
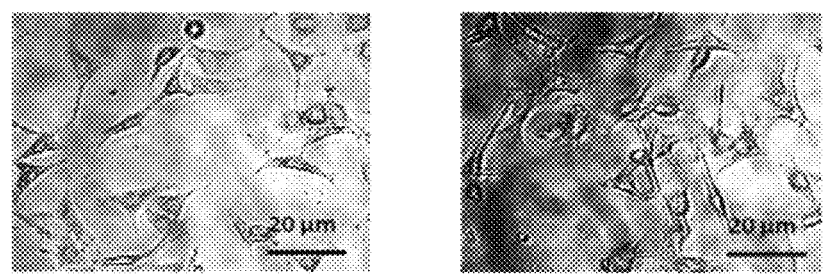
FIG. 8B depicts fluorescent photomicrographs showing uptake of GP-cPS-NPs by control NIH3T3 fibroblast cells (left) and GP phagocytosing proficient NIH3T3-D1 cells (right).

Rhodamine-labeled carboxylate polystyrene nanoparticles (cPS-Nanoparticles) were used as a model system because of their uniform narrow size distribution, high fluorescent signal, and the ability to crosslink or bind carboxylate nanoparticles to the surface of cation-modified GPs through electrostatic interactions. cPS-NPs (20 nm in diameter) were used to prepare nanoparticle cores encapsulated within the hollow cavity of GPs. The freeze-thaw cycles during the nanoparticle loading process caused nanoparticle aggregation trapping the cPS-NPs inside GPs. Additionally, the inclusion of a cationic polymer, like polyethylenimine (PEI) or chitosan electrostatically crosslinked the aggregated nanoparticles inside GPs and slowed down their release. FIG. 8 shows microscopic images of GP nanoparticle cores and receptor-targeted uptake by cells bearing glucan receptors. cPS-NPs were loaded at a concentration of $2.25 \times 10^{13}$ nanoparticles/mg GP and measurement of unbound cPS-NPs collected from washing the GP-cPS NP cores demonstrated that nanoparticle encapsulation efficiency was greater than 80%. The high cPS-NP encapsulation capacity in the hollow cavity in GPs results in the loading of >30,000, 20 nm cPS-NPs per glucan particle. However, there is a limit to the size of nanoparticles that can be encapsulated inside GPs because the average pore size in the shell of GPs is less than 40 nm. To overcome this size limitation an alternative approach was devised to bind nanoparticles to the outer GP shell.

Cationic GPs were synthesized by functionalization of the GP surface with different molecular weight, branched PEIs. The cationic PEI-GP library was prepared by reductive amination of oxidized glucan particles with PEI following similar procedures reported for other polysaccharides (T. Azzam, et al., *J. Medicinal Chemistry*, vol. 45, pp. 1817-1824, 2002). The 1,3-glycosidic bonds are stable to oxidation, thus oxidation of glucan particles takes place only at the reducing terminal glucose monomers (<2%) in the β-glucan structure of the particles. This limits the grafting of PEIs to ~0.12 μmol PEI/mg GP. The yield of periodate oxidation of the terminal glucose in the particles (60±10%) was determined using a hydroxylamine hydrochloride assay. This oxidation step limits the reaction of cationic PEIs by reductive animation to less than 0.07 μmol PEI/mg GP. Binding of the cationic polymers to the glucan particles was confirmed by a ninhydrin test. The results of PEI grafting shown in Table 1 confirmed that the levels of PEI-covalently linked to GPs ranged from 0.01 to 0.03 μmol PEI/mg GP (15-40% yield based on a maximum PEI grafting of 0.07 μmol PEI/mg GP). The molecular weight of PEI does not seem to have an effect on grafting, therefore it is likely that accessibility of the oxidized glucose units on the particle surface is the controlling parameter in the reaction.

Zeta potential results (Table 7) confirmed the synthesis of cationic GPs. Zeta potential has been previously used to follow reaction sequences on nano- and microparticles (F. Thielbeer, et al., *Bioconjugate Chemistry*, vol. 22, no. 2, pp. 144-150, 2011]. Unmodified GPs are neutral and a significant shift to a positive potential demonstrated PEI linkage to GPs. One limitation of zeta potential measurements is the effect of particle aggregation on zeta potential to establish a quantitative relation between the number of surface groups and the zeta potential values. The zeta potential results of PEI-GP samples indicate that enough PEI has been grafted on the GP surface to shift the zeta potential of neutral GPs to ~20 mV (low molecular weight PEI) or ~30 mV (high molecular weight PEI).

TABLE 7

| GP Sample | PEI surface funtionalization results μmol PEI/mg GP | Zeta Potential Peak (±5 mV) |
| --- | --- | --- |
| GP | — | 2.4 |
| 1.2k PEI-GP | 0.012 ± 0.002 | 22.1 |
| 1.8k PEI-GP | 0.031 ± 0.021 | 21.7 |
| 10k PEI-GP | 0.015 ± 0.001 | 21.1 |
| 25k PEI-GP | 0.0136 ± 0.003 | 30.2 |
| 100k PEI-GP | 0.0192 ± 0.001 | 33.3 |

Figure 7B:
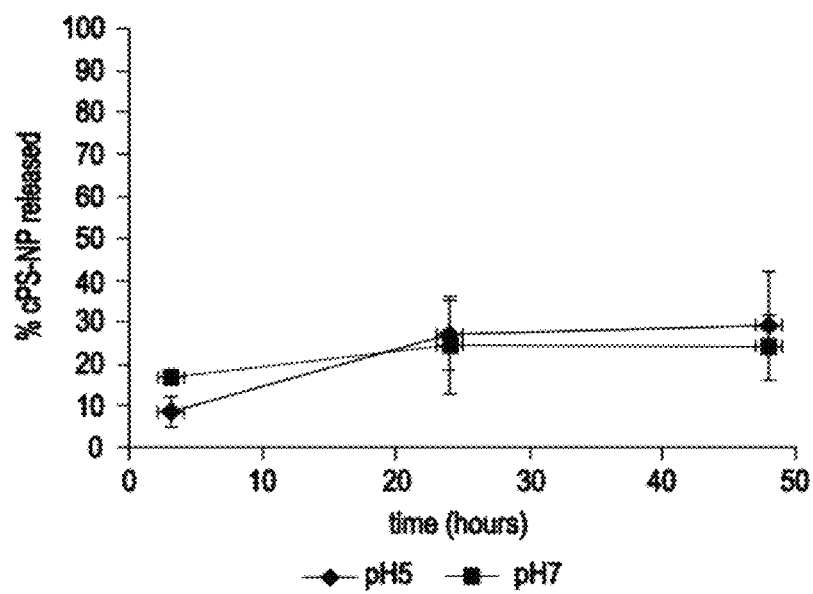
FIG. 7B depicts the stability of cPS-NP-GP. cPS-NP released from PEI-GP samples following incubation in PBS+10% FBS (pH 7) or 0.1 M acetate buffer+10% FBS (pH 5).

Fluorescent anionic carboxylate polystyrene nanoparticles (cPS-Nanoparticles) of three diameters (20, 100 and 200 nm) were used to measure the binding capacity of PEI-GPs and control GPs. Larger nanoparticles (0.5, 1, and 2 um) were also evaluated, but quantitative analysis was difficult due to spontaneous aggregation of cPS-NPs with the GPs. cPS-NP loaded GP samples prepared with nanoparticles of 200 nm or less in diameter can be separated from GPs by centrifugation. The amount of cPS-NPs bound to the GPs was measured from the fluorescence of unbound cPS-NPs collected in the supernatant and the bound nanoparticles in the NP-GP pellet fractions. The binding capacity is defined as the ratio of fluorescence emission measurements of cPS-NPs in the pellet fraction divided by the input cPS-NPs. Measured cPS-NP fluorescence in pellet/input=Binding Capacity FIG. 7 shows that the PEI-GPs readily bind cPS-NPs. The binding capacity of PEI-GPs for fluorescent anionic polystyrene nanoparticles was carried out at a ratio of 100:1 cPS-NPs:glucan particle and ranged from 50-90%. The unmodified GP control had minimal cPS-NP binding. The content of amines/GP increases with PEI molecular weight, however there is no correlation between amine content (surface charge) and binding capacity indicating that at the cPS-NP/GP ratio used in the data presented in FIG. 7 shows that the binding is limited by the nanoparticle concentration. At lower cPS-NP/GP ratio (10:1 or 1:1) binding efficiencies were higher than 95%. It was not possible to measure binding at cPS-NP/GP ratios higher than 100:1 due to inefficient separation of the excess unbound cPS-NPs from the GP pellets.

cPS-NP-PEI-GP samples were evaluated for nanoparticle binding stability at pH 5 and pH 7 in buffers containing 10% fetal bovine serum (FBS) to simulate cell uptake conditions. Fluorescence measurements of the released nanoparticles into solution and microscopic evaluation of the samples after 48 h incubation showed that more than 60% of the anionic nanoparticles remained bound to the modified PEI-GP particles (FIG. 7B). The stability of the electrostatic binding of cPS-NP to PEI-GPs provides for efficient glucan-mediated uptake of the cPS-NP-PEI-GPs into cells expressing glucan receptors (FIGS. 10 e and 10f).

Figure 9A:
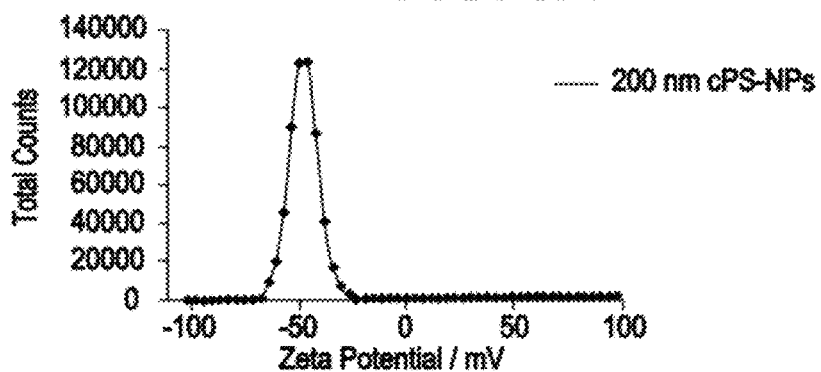
FIG. 9A depicts the Zeta potential of 200 nm anionic polystyrene NPs alone.
Figure 9B:
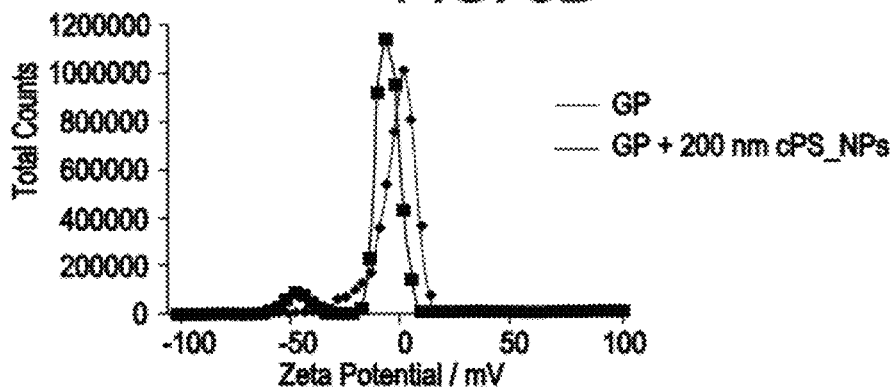
FIG. 9B depicts the Zeta potential of glucan particle (GP) control+cPS-NPs.
Figure 9C:
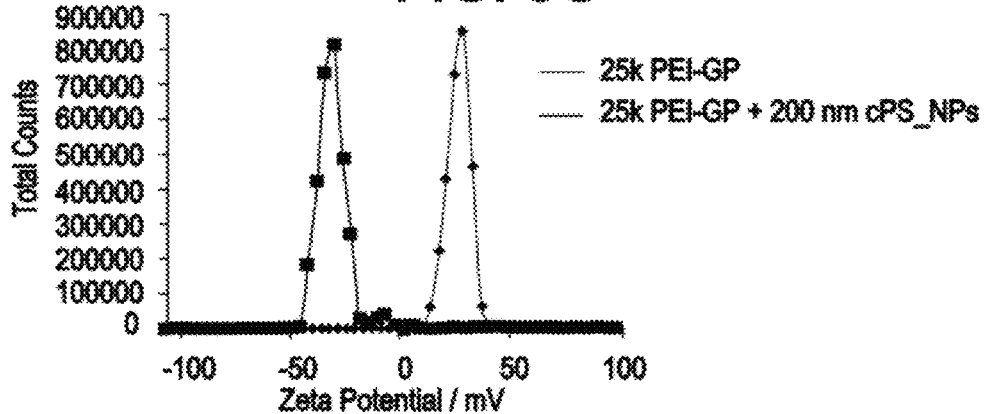
FIG. 9C depicts the Zeta potential of 25 k PEI-GP+cPS-NPs.

Zeta potential was also used to demonstrate the binding of the anionic cPS-NPs to cationic PEI-GPs. The zeta potential data in FIG. 9 shows the binding of cPS-NPs to cationic GPs as the zeta potential of the cationic GPs shift to an anionic value (−25 mV). Further, the effective separation of unbound cPS-NPs from the cPS-NP-GP sample is clear as there is only one peak (cPS-NP-GP) and no evidence of unbound cPS-NPs at ~−50 mV. In contrast, the zeta potential of the unmodified control GPs did not significantly shift following incubation with 200 nm cPS-NPs.

Figure 10A:
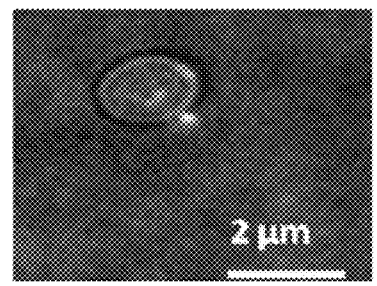
FIG. 10 depicts cPS-NPs and uptake into cells as demonstrated microscopically and via FACS analysis.
Figure 10B:
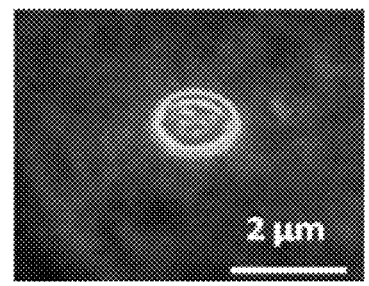
Figure 10C:
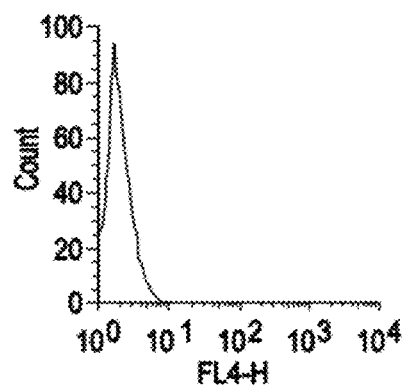
Figure 10D:
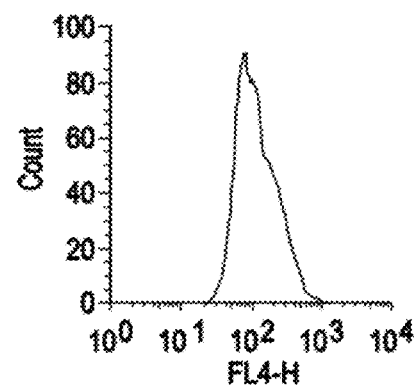
Figure 10E:
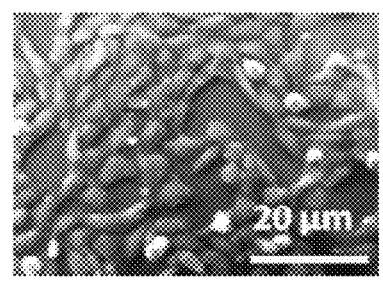
Figure 10F:
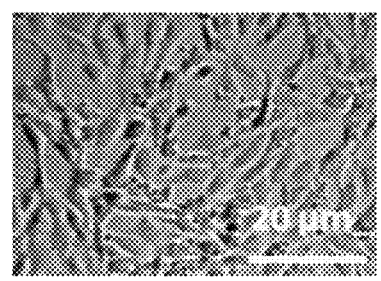

Microscopic evaluation (FIG. 10A, 10B) of these samples confirmed the binding of the fluorescent nanoparticles to the surface of PEI-GPs with the cPS-NP fluorescence localized around the perimeter of the GP shells. Unmodified control GPs did not show fluorescent cPS-NPs rosetting the GPs. Flow cytometry was used to quantitate the binding of fluorescent cPS-NPs to unmodified GP and PEI-GPs. The results, shown in FIG. 10C, 10D, confirmed the fluorescent cPS-NP binding to the PEI-modified GPs. Although the number of 200 nm nanoparticles that can be bound to the surface of modified GPs (~70 cPS-NP/GP) is significantly less than the number of 20 nm particles that can be trapped inside GPs (>30,000 20 nm cPS-NP/GP), these two NP formulation strategies allow the use of GPs for the targeted drug delivery of drug-nanoparticle conjugates over a wide range of NP sizes and surface chemistries. FIG. 10E-10F shows NIH3T3-D1 uptake of cPS-NP nanoparticles bound to 25 k PEI-GP. These particle uptake experiments demonstrate that cPS-NP electrostatically bound to PEI-GPs are more efficiently delivered to phagocytic cells than cPS-NP nanoparticles incubated with the control GP particles or free cPS-Nanoparticles. Additionally, the cell uptake experiments using cPS-NP-PEI-GP samples confirmed the stability results (FIG. 7b) of the electrostatically bound samples and that the low level of PEI surface modification of GPs, or the binding of anionic nanoparticles to the PEI-GP surface had no apparent impact on glucan-mediated phagocytosis or cellular toxicity.

Example 8

Use of Glucan Particles for the Delivery of Mesoporous Silica Nanoparticles Loaded with Doxorubicin Many types of nanoparticles have been used for drug delivery and imaging (i.e. silica nanoparticles, carbon nanotubes, gold nanoparticles, polymeric nanogels, magnetic iron oxide nanoparticles, quantum dots, PLGA nanoparticles (S. S. Suri, et al., J. Occupational Med. and Toxicol., vol. 2, pp. 1-6, 2007, R. A. Petros, et al., *Nature Reviews Drug Discovery*, vol. 9, pp. 615-627, 2010, Y. Malam, et al., *Current Medicinal Chemistry*, vol. 18, no. 7, pp. 1067-1078, 2011]). The drug can be physically trapped within nanoparticles, or chemically bound to the surface of the nanoparticles. Methods have also been developed to precisely control particle size. Mesoporous silica nanoparticles (MSN) were chosen as a model system with GPs because of their ease of synthesis and ability to trap chemotherapeutic drugs (i.e. doxorubicin). A MSN sample containing tetraethoxyorthosilicate (TEOS), amino-propyl-triethoxysilane (APTS), and 3-trihydroxysilylpropyl methylphosphonate was synthesized following the procedure reported by Tamanoi (J. Lu, et al., *Small*, vol. 3, no. 8, pp. 1341-1346, 2007, J. Lu, et al., *Nanobiotechnology*, vol. 3, pp. 89-95, 2007). The MSN was synthesized by a co-condensation method and the phosphate compound selected to have a larger alkyl chain than APTS to provide a particle with the outermost surface groups corresponding to anionic phosphate. This prevents aggregation of MSNs from inter-particle hydrogen bonding between surface silanol groups and amine groups. Successful synthesis of this MSN sample was confirmed by zeta potential (−31.1±5 mV) and DLS particle size measurements (MSN average size of 120 nm, polydispersity index PDI of 0.4). The broad particle size distribution and large particle size prevented the use of MSNs for loading inside GPs. However, the sample contained anionic phosphate groups for electrostatic binding to the surface of cationic PEI-GPs.

MSN was loaded with the chemotherapeutic doxorubicin (Dox), an anthracycline-type anti-tumor drug that exerts its antiproliferative activity via DNA intercalation and inhibition of DNA synthesis leading to cell death (G. Bonadonna, et al., *Cancer Research*, vol. 30, no. 10, pp. 2572-2582, 1970, N. P. Niraula, et al., *Applied Microbiology and Biotechnology*, vol. 87, pp. 1187-1194, 2010). Limitations in the use of Dox as an antitumor agent include chronic or acute cardiotoxicity. Dox has been studied using different nanoparticle delivery systems to enhance Dox delivery, minimize dosage and reduce toxicity leading to the successful development of a liposomal Dox formulation (Doxil).

Figure 11:
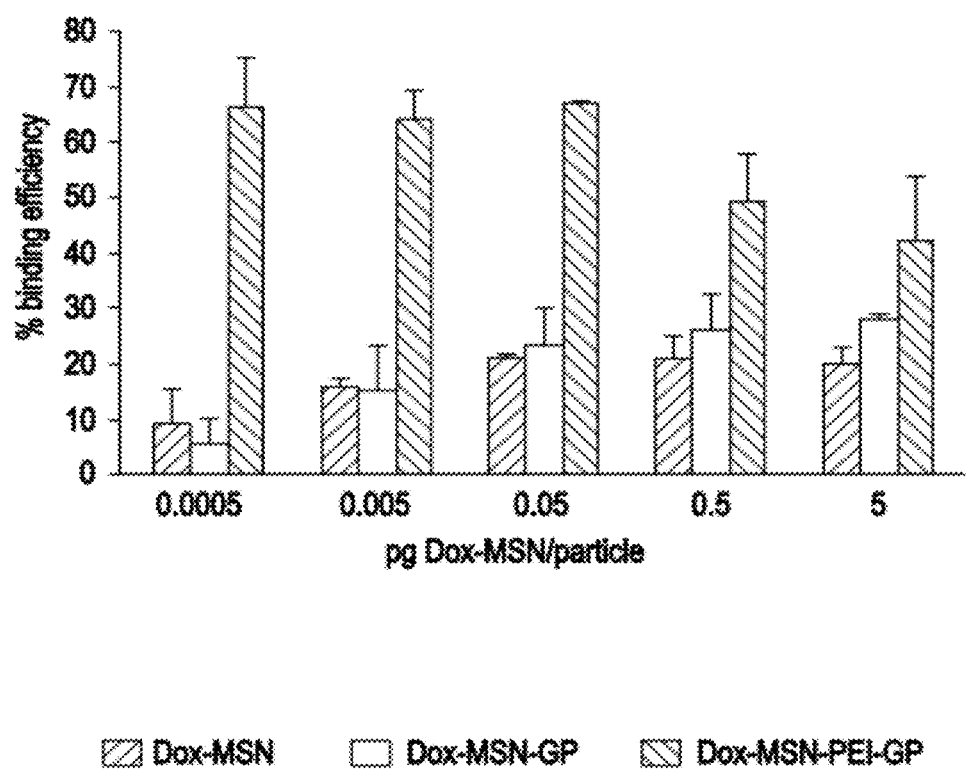
FIG. 11 depicts the binding efficiency of Dox-MSN binding to 25 k PEI-GP (the results are the average of three samples).

Dox was loaded into MSNs in DMSO at target concentrations ranging from 0-2 μmol Dox/mg MSN. Following MSN Dox loading, the Dox-MSN samples were washed to remove unbound Dox. The amount of Dox loaded into the MSN samples was quantified by measuring Dox fluorescence extracted in methanol and the results showed that the binding of Dox to MSN was 0.06 μmol Dox/mg MSN, representing 3% of the input load. This binding is ~5 times higher than Dox binding to a control MSN sample without phosphate groups. Other groups have reported similar Dox binding capacities with phosphonate functionalized MSNs (6-8% w/w) and have shown higher binding to these functionalized MSNs compared to MSN controls (H. Meng, et al., *ACSNano*, vol. 4, no. 8, pp. 4539-4550, 2010). The Dox-MSN samples were stable in PBS (pH 7) enabling the electrostatic binding of anionic Dox-MSN to the surface of cationic PEI-GPs. This binding reaction was monitored by a fluorescence binding assay (FIG. 12), zeta potential (FIG. 13) and confirmed by fluorescent microscopy (FIG. 13, inset). The fluorescence binding assay showed efficient and selective binding of Dox-MSN to PEI-GP at low Dox-MSN concentrations. Higher concentrations showed a reduction in binding efficiency likely due to saturation of available PEI for binding of Dox-MSN. The level of background binding of Dox-MSN nanoparticles to unmodified GPs corresponds to the fraction of nanoparticles that were not efficiently separated from the glucan particles. This is seen in FIG. 11, both Dox-MSN alone and Dox-MSN with GP showed similar binding as a result of measuring the fluorescence of Dox-MSN free nanoparticles in the pellet fraction. Dox-MSN-PEI-GP samples were incubated in 0.9% saline, PBS with 10% fetal bovine serum (FBS), and sodium acetate buffer (pH 5) at 37° C. for 24 h and evaluated by fluorescence microscopy to confirm stability of Dox-MSN binding to PEI-GP.

Figure 12A:
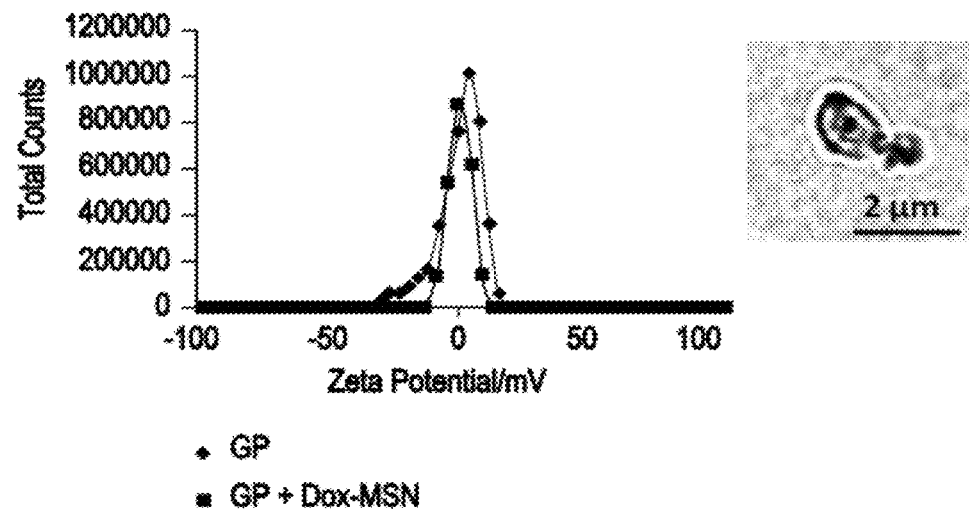
FIG. 12 depicts the Zeta potential monitoring of Dox-MSN binding to (a) GP and (b) 25 k PEI-GP. Inset; Fluorescent microscopic images of Dox-MSN bound to GP (a) and 25 k PEI-GP (b). Samples were prepared with 25 fg Dox-MSN/GP (~0.9 pg Dox/GP).
Figure 12B:
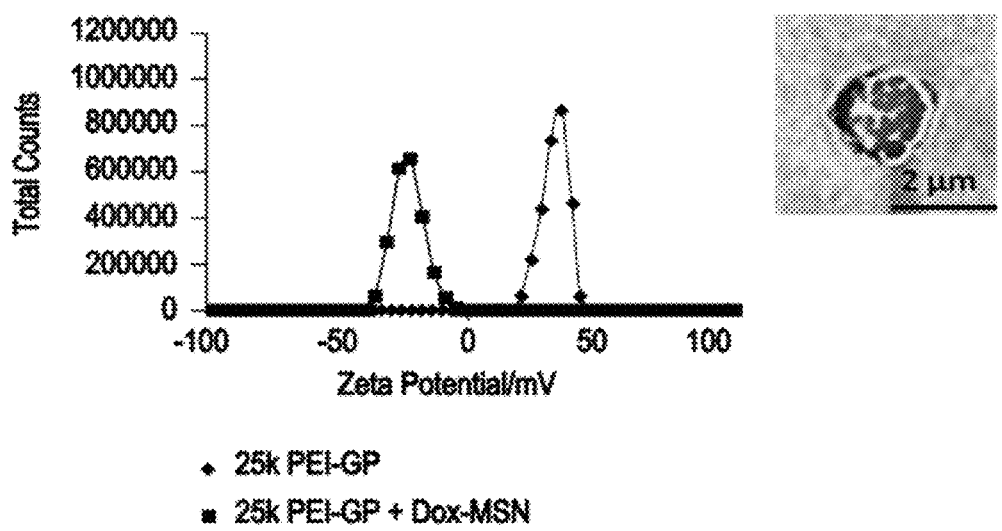
Figure 13:
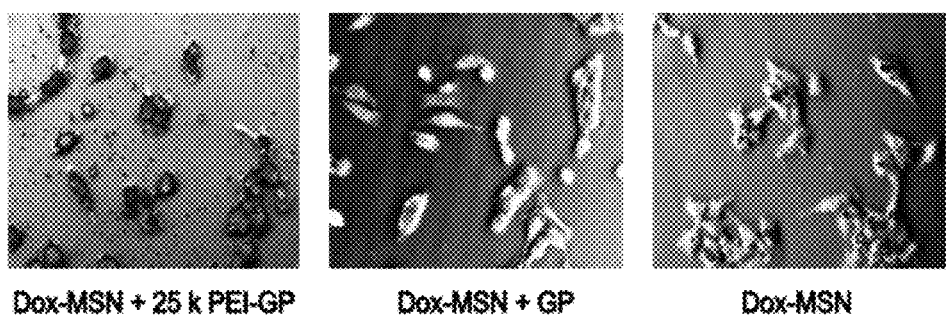
FIG. 13 depicts efficient GP-mediated Dox delivery into NIH 3T3-D1 (pictures were taken at 40× magnification).

Zeta potential measurements confirmed the selective binding of Dox-MSN to PEI-GP (FIG. 12). Dox-MSN had a negative zeta potential corresponding to the outer phosphate groups of MSN. Binding of anionic Dox-MSN to cationic PEI-GP shifted the zeta potential of the PEI-GP sample from a positive to a negative value. In comparison, the zeta potential shift of the GP sample is minimal confirming that Dox-MSN does not bind to unmodified GPs. Fluorescent microscopy confirmed that Dox-MSN binds to cationic PEI-GP but not GPs.

The Dox-MSN-GP and Dox-MSN-PEI-GP samples were tested for intracellular Dox delivery, and anti-proliferative and cytotoxic activities in the NIH 3T3-D1 cell line. This cell line has been genetically modified to express the Dectin-1 glucan receptor and efficiently phagocytoses GPs. FIG. 13 shows that Dox-MSN-PEI-GP more effectively delivered Dox into NIH3T3-D1 cells than Dox-MSN-GP or Dox-MSN after 3-hour incubation.

Figure 14:
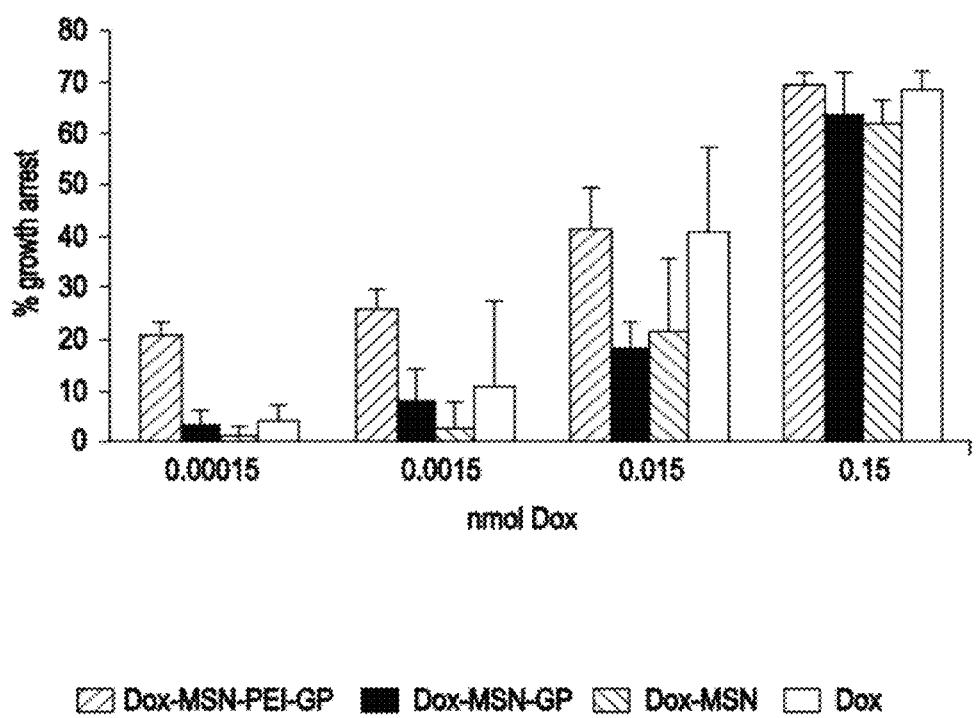
FIG. 14 depicts growth arrest of NIH 3T3-D1 cells with Dox formulations (experimental results are the average of four samples).

Cells were incubated with varying concentrations of Dox-MSN-PEI-GP, Dox-MSN-GP, free Dox-MSN, or free Dox to assess anti-proliferative and cytotoxic activities over 48 hours of incubation. Unincorporated materials were washed away after 3 hours of incubation, a sufficient period of time for efficient GP uptake by NIH 3T3-D1 cells, and the growth and viability of the cells were followed. High concentrations of free Dox or Dox-MSN (>2.5 μg Dox-MSN containing ~0.15 nmol Dox) inhibited cell growth (>60%). As seen in FIG. 14 at a concentration of 0.015 nmol Dox the Dox-MSN-PEI-GP samples showed similar effect as free Dox, but free Dox-MSN or Dox-MSN-GP samples showed less growth inhibition. Below the Minimum Inhibitory Concentration (MIC) of free Dox (0.0015 nmol Dox) there is still a significant growth inhibition (20-30%) by the Dox-MSN-PEI-GP formulation (FIG. 14) showing the increased efficacy of GP-targeted delivery of Dox-MSN-PEI-GP. Other groups have reported the use of MSN for delivery of other chemotherapeutics (i.e. camptothecin) and showed a 10-fold reduction in the drug concentration compared to free drug to achieve 50% cell death (J. Lu, et al., *Small*, vol. 3, no. 8, pp. 1341-1346, 2007, J. Lu, et al., *Nanobiotechnology*, vol. 3, pp. 89-95, 2007). The use of PEI-GP for Dox-MSN delivery allows for a reduction in drug dosage compared to free Dox or Dox-MSN demonstrating the advantage of GP targeted delivery. Future work will focus on optimization of Dox incorporation into nanoparticles and controlled release of Dox from MSN and other nanoparticles (i.e. gold nanoparticles) to improve cytotoxicity of Dox NP-GP formulations. These formulations will be evaluated in dividing tumor cells (i.e., NIH 3T3-D1) and non-dividing primary macrophages, and in co-cultivation macrophage-tumor cell assays to test the hypothesis that macrophages can act as cell-based carriers of GP-NP-Dox formulations into tumors. Optimal GP-Dox NP-GP formulations will be tested in vivo for targeted macrophage Dox delivery and accumulation in tumors.

Discussion: Examples 7 and 8

Two strategies have been developed for the targeted delivery of nanoparticles into phagocytic innate immune cells. Nanoparticles of less than 30 nm in diameter were encapsulated within the hollow cavity of GPs (~36,000 NPs/GP for 20 nm NPs). Larger anionic nanoparticles (>100 nm) were electrostatically bound to the surface of GPs derivatized with the cationic polymer PEI allowing for delivery of ~70 NPs/GP. Mesoporous silica nanoparticles (120 nm) containing doxorubicin were electrostatically bound to PEI-GPs providing for the targeted delivery of the Dox-MSN-PEI-GPs to cells capable of phagocytosing glucan particles. At Dox levels below an effective free drug concentration an equivalent amount of Dox-MSN-PEI-GPs efficiently delivered sufficient Dox to inhibit the growth of the GP-phagocytic cell line NIH 3T3-D1. These results demonstrate that the NP-GP delivery system offers the potential of GP-mediated macrophage-targeted delivery of multiple nanoparticles in a single uptake event providing for high efficiency intracellular drug delivery. It is believed that macrophages can serve as "Trojan horses" carrying and releasing the drug into solid tumors may further enhance the in vivo Dox-MSN-PEI-GP anti-tumor effect. A variety of drug loaded nanoparticulate formulations are possible that may provide advantages of higher drug binding capacity and the possibility of controlled release. In addition the use of certain types of nanoparticles (i.e. gold nanoparticles, magnetic iron oxide) may add theranostic properties to the NP-GP delivery system.

Example 9

Cell Purification with Magnetic GP Samples

Figure 15:
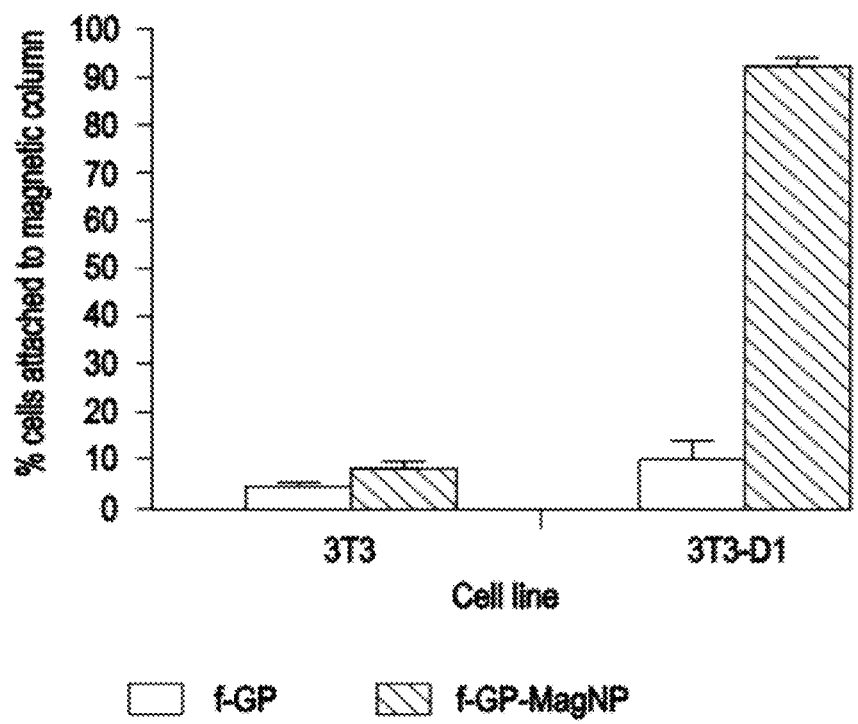
FIG. 15 depicts the % of 3T3 or 3T3-D1 cells (into which fGP-mag-NPs are incorporated) purified by attachment to a magnetic column.

The NIH3T3 and dectin-1 receptor expressing 3T3-D1 cell lines were plated in 6-well plates to obtain a cell density of $5 \times 10^5$ cells/well on the day of the experiment. Particle suspensions (fluorescently labeled magnetic Glucan Particles (GPs) and fluorescently labeled non-magnetic GPs) at a concentration of $1 \times 10^8$ particles/mL were resuspended by sonication to single particles. 50 µL of the particle suspension was added to the cells (10:1 particle to cell ratio) and the samples were incubated overnight at 37° C. The media was removed and the cells were washed once with sterile PBS. The PBS was carefully removed and 1 mL of PBS with 50 µL of trypsin EDTA was added to each well. The cells were incubated with trypsin-EDTA for 2-3 minutes to detach the cells from the plate and the suspended cells transferred to Eppendorf tubes. The cells were centrifuged for 10 min at 1000 rpm, liquid removed and the samples resuspended in 500 µL of column buffer (PBS, pH 7.2 containing 0.5% BSA and 2 mM EDTA). The samples were transferred to magnetic purification columns (MACS separation columns, Miltenyi Biotec Inc, Auburn, Calif.) and the flow-through buffer containing cells without magnetic particles was collected. The columns were washed three times with the column buffer to remove any cells without magnetic particles. The columns were removed from the magnet to release the cells containing magnetic particles and these cells were collected by washing the column three times with the buffer solution. Both the bound and unbound fractions were centrifuged for 10 min at 1000 rpm, the solvent carefully removed and the cells resuspended in 1 mL of buffer. Samples of 10 µL were mixed with 10 µL of 0.2% trypan blue and the cells evaluated for viability and counted using a hematocytometer. FIG. 15 depicts the % of cells attached to the magnetic column. fGP-mag-NPs were quite efficiently taken up by glucan receptor expressing 3T3-D1 cells and served as an effective means to purify cells via magnetic separation.

Materials and Methods used throughout the Examples, in particular, in Examples 7-8 are as follows. Such detailed Materials and Methods are exemplary and are not intended to be limiting.

1.1. Materials.

Carboxylate modified red fluorescent nanoparticles and Alamar Blue were purchased from Invitrogen (Carlsbad, Calif.); glucan particles (GP) were prepared from Baker's yeast (Fleishmans Baker's yeast, AB Mauri Food Inc, Chesterfield Mo.) according to a previously published procedure (E. Soto, et al., *Bioconjugate Chemistry*, vol. 19, no. 4, pp. 840-848, 2008). Polyethylenimines (PEIs, molecular weight of 1.2, 10 and 100 kDa) were purchased from Polysciences (Warrington, Pa.). All other PEIs, chemicals for the synthesis of MSNs, and solvents were purchased from Sigma Aldrich (Allentown, Pa.) and used as received. Materials for cell tissue culture experiments were purchased from Gibco Scientific (Grand Island, N.Y.) or Fisher Scientific (Fairlawn, N.J.).

1.2. Preparation of 20 nm Nanoparticle Cores Inside GPs.

Fluorescent 20 nm nanoparticles were used at a concentration of $4.5 \times 10^{15}$ particles/mL. Dry glucan particles were mixed with 5 µL nanoparticle suspension/mg GP to obtain a uniform paste, incubated at room temperature for 1 h and the GP-NP loaded formulation was lyophilized. This hydration-loading-lyophilization procedure was repeated using water (5 µL/mg GP) to hydraulically push nanoparticles into GPs by capillary action. The dry GP-NPs were hydrated and washed after the second lyophilization to remove free nanoparticles, sterilized in 70% ethanol at −20° C., aseptically washed three times with 0.9% saline, resuspended in 0.9% saline, counted with a hematocytometer, and GP concentration adjusted to a concentration of $1 \times 10^8$ particles/mL. Samples were evaluated by fluorescence microscopy, flow cytometry, zeta potential, and for GP mediated uptake into phagocytic cells.

1.3. Synthesis of Cationic GPs.

GPs (5 mg) were resuspended in 10 mLs of water by homogenization. Potassium periodate (0.4 mL of a 1 mg/mL solution) was added and the mixture stirred in the dark at room temperature for at least six hours. Oxidized GP samples were washed three times with water, and used immediately for reductive amination synthesis. Cationic polymers (PEIs) and water were added to the oxidized GP samples (1 µmol PEI/mg GP) and the particles were resuspended and mixed at room temperature overnight. The aminated samples were reduced with sodium borohydride (0.1 g) and incubated at room temperature for 48 hours. The reduced samples were washed with water. Tris buffer (5 mLs, pH 7.5, 0.05 M) was added and the sample incubated for 30 minutes. The samples were washed with water, resuspended in 70% ethanol and stored overnight at −20° C. for sterilization, then aseptically washed three times with 0.9% saline, resuspended in 0.9% saline, particles counted with a hematocytometer and the particle suspensions diluted to a concentration of $1 \times 10^8$ particles/mL and stored at −20° C.

Periodate oxidized glucan particles (n=5 samples) were evaluated for aldehyde content using a hydroxylamine hydrochloride assay (H. Zhao, et al., *Pharmaceutical Research*, vol. 8, pp. 400-402, 1991). Oxidized GP samples (5 mg) were incubated in 1 mL of DMSO at 50° C. for 2 h to dissolve the particles. The samples were centrifuged to remove insoluble material (chitin). Hydroxylamine hydrochloride solution (0.5 mL, 0.5 N) containing 0.05% w/v methyl orange was added to the samples and the mixture was incubated at room temperature for 4 hours. The samples were titrated with a standardized 0.01 M sodium hydroxide solution until a red-to-yellow end point was achieved.

The level of PEI coupling in the PEI-GP samples was measured with a ninhydrin assay. PEI-GP samples (1 mg) were resuspended in 100 µL of water and mixed with 100 µL of 2% w/v ninhydrin in DMSO. The samples were heated at 100° C. for 20 min, cooled to room temperature and 800 µL of ethanol was added. PEI samples of different concentrations were also treated with ninhydrin to prepare calibration curves and determine the linear response range of each of the PEIs used in the chemical modification of GPs. Absorbance was measured at 570 nm for the calibration curve controls, PEI-GP samples and blank GP controls. A total of three samples of each PEI-GP were analyzed with the ninhydrin assay.

1.4. Binding of Nanoparticles to Surface Derivatized GPs.

GP or PEI-GP samples (10 µL 1×10$^8$ part/mL), and rhodamine labeled carboxylated nanoparticles of different diameter (20, 100 and 200 nm) were mixed at NP/GP ratios of 1/1, 10/1 and 100/1 in a final volume of 100 µL in 0.9% saline. The samples were incubated in the dark for 1 hour and the unbound nanoparticles separated from the GPs containing bound nanoparticles by centrifugation (10000 rpm for 2 min). The samples were then washed with 0.9% saline (100 µL) to remove unbound nanoparticles from the pellet, washed pellet samples resuspended in 0.9% saline (100 µL) and fluorescence of the carboxylate polystyrene nanoparticles (excitation=580 nm, emission=605 nm) measured in all fractions to quantify bound and unbound nanoparticles. The average of at least five measurements was collected for each experimental condition. NP-GP samples were also evaluated by zeta potential measurements, flow cytometry, and fluorescence microscopy. The NP-GP samples were evaluated for nanoparticle binding stability to GPs by incubation in phosphate buffer saline (PBS, pH 7) containing 10% fetal bovine serum (FBS), or sodium acetate buffer (0.1 M, pH 5) over 48 hours. The samples were processed by centrifugation to remove free nanoparticles, washed and supernatant fractions analyzed for released cPS-NPs, and pelleted fractions evaluated by fluorescence microscopy to assess binding of cPS-NPs to GPs.

1.5. Mesoporous Silica Nanoparticles (MSNs).

MSN samples containing phosphate and amine functional groups were prepared by the co-condensation method reported by Tamanoi (J. Lu, et al., *Small*, vol. 3, no. 8, pp. 1341-1346, 2007, J. Lu, et al., *Nanobiotechnology*, vol. 3, pp. 89-95, 2007). A solution containing cetyl trimethylammonium bromide (CTAB, 0.5 g) in water (24 mLs) and NaOH (2 M, 0.2 mL) was heated to 80° C. and stirred vigorously until the solutes were dissolved. A solution containing the MSN reagents (tetraethylorthosilicate, TEOS (2.5 mLs) and aminopropyltriethoxysilane, APTS (12 µLs)) were then added and the mixture stirred at 80° C. for 15 minutes. 3-trihydroxysilylpropyl methylphosphonate (0.63 mL) was added and the solution was incubated for 2 hours at 80° C. with stirring. The solution was cooled to room temperature and then centrifuged (3,000 g for 20 minutes), washed with 50 mLs of methanol and dried at room temperature. The CTAB was extracted from the MSN by refluxing the particles (850 mg) in an acidic methanol mixture (90 mLs of methanol and 5 mLs of 12.1 M HCl) for 24 hours. The particles were then washed three times with 50 mLs of methanol and left to dry overnight.

MSN samples were characterized by dynamic light scattering (DLS) particle size measurements, and zeta potential.

1.6. Doxorubicin Binding to MSN.

MSN suspensions and doxorubicin (0-2 µmol Dox/mg MSN) were incubated in 1 mL of DMSO overnight at room temperature. The samples were then centrifuged and the supernatant removed. The Dox-MSN pellets were lyophilized and washed three times with 1 mL of water to remove Dox bound on the outside of MSN. A total of five Dox-MSN samples were prepared for each Dox loading concentration. Dox-MSN samples were resuspended in sterile water at a concentration of 1 mg/mL and stored at −20° C. The amount of Dox bound to MSN was quantified by incubating 0.2 mg samples of Dox-MSN in methanol (1 mL) overnight at room temperature to completely extract Dox. Doxorubicin was quantified by fluorescence spectroscopy (excitation=480 nm, emission=550 nm).

1.7. Synthesis of Dox-MSN-PEI-GP.

25 k PEI-GPs, unmodified GPs (10 µL 1×10$^8$ particles/mL) and Dox-MSN nanoparticles (10 µL, 5×10$^{-5}$ to 5×10$^{-2}$ mg Dox-MSN/mL) were mixed at a final volume of 100 uL in 0.9% saline. The concentration range of Dox-MSN allowed studying binding to PEI-GP at Dox-MSN/PEI-GP ratios from 0.0005 to 5 pg Dox-MSN/GP. The samples were incubated in the dark for 1 hour at room temperature and the unbound Dox-MSN separated from the PEI-GP or GPs containing bound nanoparticles by centrifugation (10000 rpm for 2 min). Additional control samples containing only Dox-MSN were processed in the purification procedure. The samples were then washed with 0.9% saline (100 µL) to remove unbound nanoparticles from the pellet, washed pellet samples resuspended in 0.9% saline (100 uL) and fluorescence of doxorubicin measured in all fractions to quantify amount of bound and unbound Dox-MSN. The average of at least three measurements was collected for each experimental condition. Dox-MSN-PEI-GP and Dox-MSN-GP samples were also evaluated by zeta potential measurements, and fluorescence microscopy. The samples were evaluated for stability by incubation in phosphate buffer saline (PBS, pH 7) containing 10% fetal bovine serum (FBS), or sodium acetate buffer (0.1 M, pH 5) over 48 hours. At various time points samples were processed by centrifugation to remove free nanoparticles, washed and supernatant fractions analyzed by fluorescence spectroscopy to quantify released Dox, and pellet fractions were analyzed by fluorescence microscopy to confirm stability of Dox-MSN-PEI-GP samples.

1.8. Dynamic Light Scattering (DLS) and Zeta Potential Measurements.

Size and zeta potential of nanoparticle samples, and zeta potential of GP/NP samples were determined with a Malvern Zetasizer Nano-ZS (Malvern Instruments, Worcestershire, UK). Solvents and buffers were filtered through 0.22 µm filters before sample preparation. A suspension of particles (1 mg/mL for nanoparticle samples, 2×10$^6$ particles/mL for GP samples) was diluted in 1 mL of 20 mM Hepes buffer, vortexed and transferred to a 1 mL clear zeta potential cuvette (DTS 1061, Malvern). Zeta potential was collected at 25° C. from −150 to +150 mV. The results are the average three samples. For each sample a total of 30 measurements were collected and analyzed with the Dispersion Technology software 4.20 (Malvern) producing diagrams of zeta potential distribution versus total counts. DLS measurements were obtained from samples in the same zeta potential cells at 25° C. The average of 20 measurements/sample was collected in the size range from 1 nm to 10000 nm. The data were analyzed with the Dispersion Technology software producing histograms for particle size versus % intensity.

1.9. Flow Cytometry (FACS).

FACS measurements were obtained using a Becton Dickinson FACSCalibur instrument (BD, Franklin Lakes, N.J.). Samples were prepared for FACS analysis by binding of $2\times10^7$ nanoparticles to $2\times10^6$ GP particles. The bound NP-GP samples were washed from unbound nanoparticles and resuspended at $2\times10^6$ GP/mL in PBS. Unmodified GPs were used as negative control and rhodamine-labeled GPs as the positive control. The particles were analyzed with an FL4 laser at 605 nm by collecting an average of 15000 measurements. Gating and analysis was performed using FlowJo 6.4.2 software.

1.10. Dox-MSN/GP Cell Delivery.

Dox-MSN samples were prepared as described in section 2.6. Dox-MSN samples were bound to 25 k PEI-GP or unmodified GP particles as described in section 2.7. The samples were prepared by binding $0-5\times10^{-4}$ mg Dox-MSN/$1\times10^6$ PEI-GP or GPs, equivalent to 0-5 pg Dox-MSN/glucan particle. The amount of PEI-GP or GP particles was chosen to test for cell uptake at a 10:1 GP:cell ratio to maximize phagocytic cell uptake. Based on the binding of Dox to Dox-MSN, the Dox-MSN-PEI-GP samples contained 0-0.15 nmol Dox. Dox-MSN free nanoparticles and soluble Dox (free Dox) were also evaluated in the same concentration range. These samples were evaluated for cellular uptake and Dox delivery using the NIH3T3-D1 cell line. This cell line was derived from the NIH3T3 fibroblast cell line by integration of the dectin-1 gene to produce cells expressing the $\beta$-1,3-D-glucan receptor dectin-1 allowing for efficient GP phagocytosis (J. A. Willment, et al., *Journal of Biological Chemistry*, vol. 276, pp. 43818-43823, 2001, A. S. Marshall, et al., *Journal of Biological Chemistry*, vol. 279, pp. 14792-14802, 2004). Samples were resuspended in complete DMEM medium (250 µL) and added to 24 well plates containing $1\times10^5$ cells in 0.5 mL complete DMEM medium. After incubation for 3 hours at 37° C. under 5% $CO_2$ the cells were fixed with 1% formalin and observed microscopically for fluorescent Dox-MSN/PEI-GP phagocytosis. To determine the effects of Dox-MSN/PEI-GP, Dox-MSN or free Dox on cell growth and viability these samples were incubated for 3 hours with cells as described above, and the cell monolayers were washed in complete DMEM and incubated for an additional 48 hours. Alamar blue (50 µL) was added, the cells incubated at 37° C. for 2 hrs and fluorescence was measured, excitation wavelength=530 nm, emission wavelength=590 nm. Fluorescent response is dependent on the reduction of the Alamar Blue indicator by metabolically active cells and is an indicator of cell number and viability. Growth arrest was calculated from the fluorescence response of the sample wells relative to the response of control wells containing cells incubated in the absence of doxorubicin. The results are the average of four samples prepared for each Dox-MSN formulation evaluated for NIH3T3-D1 growth arrest.

The present invention and its embodiments have been described in detail. However, the scope of the present invention is not intended to be limited to the particular embodiments of any process, manufacture, composition of matter, compounds, means, methods, and/or steps described in the specification. Various modifications, substitutions, and variations can be made to the disclosed material without departing from the spirit and/or essential characteristics of the present invention. Accordingly, one of ordinary skill in the art will readily appreciate from the disclosure that later modifications, substitutions, and/or variations performing substantially the same function or achieving substantially the same result as embodiments described herein can be utilized according to such related embodiments of the present invention. Thus, the following claims are intended to encompass within their scope modifications, substitutions, and variations to processes, manufactures, compositions of matter, compounds, means, methods, and/or steps disclosed herein.

The contents of any patents, patent applications, and references cited throughout the specification are herein incorporated by reference in their entireties.

The invention claimed is:

1. A method for making a YCWP-NP delivery system, comprising yeast cell wall particles (YCWPs) comprising nanoparticles (NPs) having at least one dimension of about 1-40 nm contained within the interior of the YCWPs, the method comprising the steps of:
    (a) loading the NPs into the YCWPs, wherein the loading comprises incubating a suspension comprising YCWPs and NPs for a time sufficient for the NPs to enter into the YCWPs,
    (b) drying the material resulting from (a),
    (c) optionally repeating steps (a)-(b) at least once,
    (d) resuspending the YCWPs and nanoparticles in a solvent for a time sufficient for additional NPs to enter into the YCWPs,
    (e) optionally drying the material resulting from (d), and
    (f) optionally trapping the NPs in the YCWPs using an appropriate trapping means, such that the YCWP-NP delivery system is made;
    wherein the NPs are insoluble in water.

2. The method of claim 1, wherein the NPs have at least one dimension of about 2-40 nm.

3. The method of claim 1, wherein the NPs have at least one dimension of about 5-30 nm.

4. The method of claim 1, wherein the NPs have at least one dimension of about 10-30 nm.

5. The method of claim 1, wherein the YCWPs are selected from the group consisting of YGPs, YGMPs, YCPs and YGCPs.

6. The method of claim 5, wherein the YCWPs are YGPs.

7. The method of claim 1, wherein the loading comprises incubating the suspension for about 1-2 hours.

8. The method of claim 1, wherein the solvent is saline or water.

9. The method of claim 1, wherein the nanoparticles are selected from the group consisting of quantum dots, gold particles and magnetic particles.

10. The method of claim 1, wherein the trapping means is selected from the group consisting of a physical trapping means, an electrostatic trapping means, an affinity trapping means, and a hydrophobic trapping means.

11. The method of claim 1, wherein the trapping means is an electrostatic trapping means.

12. The method of claim 11, wherein the electrostatic trapping results from interaction of an anionic nanoparticle with a cationic polymeric trapping molecule or of a cationic nanoparticle with an anionic polymeric trapping molecule.

13. The method of claim 1, wherein the trapping means is physical trapping.

14. The method of claim 13, wherein the physical trapping results from interaction of the nanoparticle with a trapping molecule selected from the group consisting of alginate and chitosan.

15. The method of claim 12, wherein the interaction is of the anionic nanoparticle with the cationic polymeric trapping molecule and wherein the cationic polymeric trapping molecule comprises polyethyleneimine, polylysine, chitosan, or protamine.

* * * * *